United States Patent
Ishii et al.

(10) Patent No.: US 9,447,013 B2
(45) Date of Patent: Sep. 20, 2016

(54) METHOD FOR PRODUCING OXIDE

(71) Applicant: DAICEL CORPORATION, Osaka-shi, Osaka (JP)

(72) Inventors: Yasutaka Ishii, Takatsuki (JP); Ichiro Takase, Himeji (JP); Yoshiya Narasaki, Himeji (JP); Takamasa Suzuki, Himeji (JP)

(73) Assignee: DAICEL CORPORATION, Osaka-shi (JP)

( * ) Notice: Subject to any disclaimer, the term of this patent is extended or adjusted under 35 U.S.C. 154(b) by 0 days.

(21) Appl. No.: 14/905,329

(22) PCT Filed: Jul. 14, 2014

(86) PCT No.: PCT/JP2014/068704
§ 371 (c)(1),
(2) Date: Jan. 15, 2016

(87) PCT Pub. No.: WO2015/008729
PCT Pub. Date: Jan. 22, 2015

(65) Prior Publication Data
US 2016/0159722 A1   Jun. 9, 2016

(30) Foreign Application Priority Data
Jul. 18, 2013 (JP) .................. 2013-149855

(51) Int. Cl.
*C07C 51/16* (2006.01)
*C07C 51/34* (2006.01)
(Continued)

(52) U.S. Cl.
CPC ............. *C07C 51/34* (2013.01); *B01J 19/24* (2013.01); *C07C 29/48* (2013.01); *C07C 45/33* (2013.01); *C07C 45/40* (2013.01); *C07C 51/215* (2013.01); *B01J 2219/24* (2013.01); *Y02P 20/55* (2015.11)

(58) Field of Classification Search
CPC ....... C07C 51/34; C07C 29/48; C07C 45/33; C07C 45/40; C07C 51/215; B01J 19/24

USPC ........................................ 562/412
See application file for complete search history.

(56) References Cited

U.S. PATENT DOCUMENTS

| | | |
|---|---|---|
| 5,030,739 A | 7/1991 | Foricher et al. |
| 7,183,423 B1 | 2/2007 | Ishii et al. |

(Continued)

FOREIGN PATENT DOCUMENTS

| | | |
|---|---|---|
| EP | 0 198 351 A2 | 10/1986 |
| EP | 1 055 654 A1 | 11/2000 |

(Continued)

OTHER PUBLICATIONS

International Search Report, issued in PCT/JP2014/068704, dated Sep. 2, 2014.

(Continued)

*Primary Examiner* — Deborah D Carr
(74) *Attorney, Agent, or Firm* — Birch, Stewart, Kolasch & Birch, LLP

(57) ABSTRACT

Provided is a method of oxidizing a substrate with excellent oxidizing power to yield a corresponding oxide. The method can employ a commercially available imide compound as intact as a catalyst and can produce the oxide in a high yield under mild conditions.

A method for producing an oxide according to the present invention includes performing oxidation of a substrate in the presence of oxygen and ozone under catalysis of an imide compound to yield a corresponding oxide. The imide compound has a cyclic imide skeleton represented by Formula (I). In the formula, n is selected from 0 and 1; and X is selected from an oxygen atom and an —OR group, where R is selected from hydrogen and a hydroxy-protecting group.

[Chem. 1]

(I)

20 Claims, 3 Drawing Sheets

(51) Int. Cl.
*C07C 45/33* (2006.01)
*C07C 45/40* (2006.01)
*C07C 51/215* (2006.01)
*B01J 19/24* (2006.01)
*C07C 29/48* (2006.01)

(56) References Cited

U.S. PATENT DOCUMENTS

2002/0128149 A1 9/2002 Ishii et al.
2006/0036100 A1 2/2006 Ishii et al.

FOREIGN PATENT DOCUMENTS

| | | |
|---|---|---|
| EP | 1 238 704 A2 | 9/2002 |
| JP | 61-238733 A | 10/1986 |
| JP | 8-38909 A | 2/1996 |
| JP | 9-327626 A | 12/1997 |
| JP | 2001-26562 A | 1/2001 |
| JP | 2002-226422 A | 8/2002 |
| JP | 2002-331242 A | 11/2002 |
| JP | 2003-321413 A | 11/2003 |
| WO | WO 00/35835 A1 | 6/2000 |

OTHER PUBLICATIONS

Written Opinion of the International Searching Authority, issued in PCT/JP2014/068704, dated Sep. 2, 2014.

METHOD FOR PRODUCING OXIDE

TECHNICAL FIELD

The present invention relates to a method for oxidizing a substrate in the presence of oxygen and ozone under catalysis of an imide compound. The application claims priority to Japanese Patent Application No. 2013-149855 filed to Japan on Jul. 18, 2013, the entire contents of which are incorporated herein by reference.

BACKGROUND ART

Oxidation reactions are one of the most basic reactions in the organic chemical industry, for which various oxidation methods have been developed. Patent Literature (PTL) 1 describes a method for oxidizing a compound capable of forming a radical typically with molecular oxygen under catalysis of a lipid-soluble imide compound. Disadvantageously, however, the method fails to use a commercially available imide compound as intact as a catalyst, the method uses the lipid-soluble imide compound that is hardly prepared by synthesis, and the method suffers from a very low yield when normal alkanes (linear alkanes) are used as the substrate even when the lipid-soluble imide compound that is hardly prepared by synthesis is used.

CITATION LIST

Patent Literature

PTL 1: Japanese Unexamined Patent Application Publication (JP-A) No. 2002-331242

SUMMARY OF INVENTION

Technical Problem

Accordingly, the present invention has an object to provide a method for producing an oxide by oxidizing a substrate with excellent oxidizing power to yield the corresponding oxide, where the method can use a commercially available imide compound as intact as a catalyst and can produce the oxide in a high yield under mild conditions.

The present invention has another object to provide a method for oxidizing a substrate with excellent oxidizing power, where the method can use a commercially available imide compound as intact as a catalyst and can oxidize the substrate under mild conditions with a high conversion.

Solution to Problem

After the intensive investigations to achieve the objects, the inventors of the present invention have found that oxygen, when used as an oxidizer in coexistence with ozone, can activate radical reactions because ozone effectively promotes the abstraction of hydrogen from the substrate; and that this configuration allows the oxidation of a substrate with a high conversion under mild conditions to yield a corresponding oxide in a high yield, even when a commercially available imide compound is used as intact as a catalyst and/or even when a normal alkane, which is resistant to oxidation, is used as the substrate. The present invention has been made based on these findings.

Specifically, the present invention provides, in an embodiment, a method for producing an oxide. The method includes performing oxidation of a substrate (A) in the presence of oxygen and ozone under catalysis of an imide compound to yield a corresponding oxide. The imide compound contains a cyclic imide skeleton represented by Formula (I):

[Chem. 1]

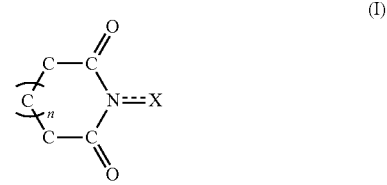

where n is selected from 0 and 1; and X is selected from an oxygen atom and an —OR group, where R is selected from hydrogen and a hydroxy-protecting group. The substrate (A) is a compound selected from the group consisting of (A1) compounds containing a heteroatom and a carbon-hydrogen bond at an adjacent position to the heteroatom, (A2) compounds containing a carbon-heteroatom double bond, (A3) compounds containing a methine carbon atom, (A4) compounds containing an unsaturated bond and a carbon-hydrogen bond at an adjacent position to the unsaturated bond, (A5) alicyclic compounds, (A6) conjugated compounds, (A7) amine compounds, (A8) aromatic compounds, (A9) normal alkanes, and (A10) olefins.

In the oxide production method, a metallic compound may be used as a promoter in combination with the imide compound as the catalyst.

In the oxide production method, the metallic compound may include at least one metal element selected from the group consisting of cobalt, manganese, zirconium, and molybdenum.

In the oxide production method, the oxidation as a reaction may be performed using approximately no solvent.

In the oxide production method, the oxidation as a reaction may be performed under normal atmospheric pressure.

In the oxide production method, the oxidation as a reaction may be performed in the presence of at least one selected from the group consisting of nitric acid and nitrogen oxides.

In the oxide production method, the oxidation as a reaction may be performed at a temperature of 100° C. or lower.

The present invention further provides, in another embodiment, a method for oxidizing a substrate. The method includes oxidizing a substrate (A) in the presence of oxygen and ozone under catalysis of an imide compound. The imide compound contains a cyclic imide skeleton represented by Formula (I):

[Chem. 2]

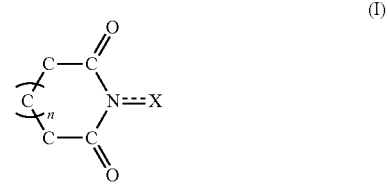

where n is selected from 0 and 1; and X is selected from an oxygen atom and an —OR group, where R is selected from hydrogen and a hydroxy-protecting group. The substrate (A) is a compound selected from the group consisting of (A1)

compounds containing a heteroatom and a carbon-hydrogen bond at an adjacent position to the heteroatom, (A2) compounds containing a carbon-heteroatom double bond, (A3) compounds containing a methine carbon atom, (A4) compounds containing an unsaturated bond and a carbon-hydrogen bond at an adjacent position to the unsaturated bond, (A5) alicyclic compounds, (A6) conjugated compounds, (A7) amine compounds, (A8) aromatic compounds, (A9) normal alkanes, and (A10) olefins.

Specifically, the present invention relates to followings:

(1) A method for producing an oxide. The method includes performing oxidation of a substrate (A) in the presence of oxygen and ozone under catalysis of an imide compound to yield a corresponding oxide. The imide compound contains a cyclic imide skeleton represented by Formula (I).

The substrate (A) is a compound selected from the group consisting of (A1) compounds containing a heteroatom and a carbon-hydrogen bond at an adjacent position to the heteroatom, (A2) compounds containing a carbon-heteroatom double bond, (A3) compounds containing a methine carbon atom, (A4) compounds containing an unsaturated bond and a carbon-hydrogen bond at an adjacent position to the unsaturated bond, (A5) alicyclic compounds, (A6) conjugated compounds, (A7) amine compounds, (A8) aromatic compounds, (A9) normal alkanes, and (A10) olefins.

(2) In the oxide production method according to (1), a metallic compound may be used as a promoter in combination with the imide compound as the catalyst.

(3) In the oxide production method according to (2), the metallic compound may include at least one metal element selected from the group consisting of cobalt, manganese, zirconium, and molybdenum.

(4) In the oxide production method according to (2), the metallic compound may be an organic acid salt of at least one metal element selected from the group consisting of cobalt, manganese, zirconium, and molybdenum.

(5) In the oxide production method according to any one of (1) to (4), the oxidation as a reaction may be performed using approximately no solvent.

(6) In the oxide production method according to any one of (1) to (5), the oxidation as a reaction may be performed under normal atmospheric pressure.

(7) In the oxide production method according to any one of (1) to (6), the oxidation as a reaction may be performed in the presence of at least one selected from the group consisting of nitric acid and nitrogen oxides.

(8) In the oxide production method according to any one of (1) to (7), the oxidation as a reaction may be performed at a temperature of 100° C. or lower.

(9) In the oxide production method according to any one of (1) to (8), the substrate (A) may be a compound selected from the group consisting of (A3-2) chain compounds containing a methine carbon atom, (A4-1) aromatic compounds containing an aromatic ring and a methyl and/or methylene group at an adjacent position to the aromatic ring, and (A9) normal alkanes.

(10) In the oxide production method according to any one of (1) to (8), the substrate (A) may be a compound selected from the group consisting of normal alkanes, branched chain alkanes, and aromatic hydrocarbons.

(11) In the oxide production method according to any one of (2) to (10), the metallic compound may be intermittently fed in an amount of 0.005 to 0.500 moles per mole of the imide compound.

(12) In the oxide production method according to any one of (1) to (11), the oxidation as a reaction may be performed under flow of oxygen gas and ozone gas (the oxygen gas and the ozone gas may flow at a flow rate of 1 to 40 L/min. per mole of the substrate (A)).

(13) In the oxide production method according to any one of (1) to (12), the oxidation as a reaction may be performed with bubbling of oxygen gas and ozone gas.

(14) In the oxide production method according to any one of (1) to (13), the imide compound may be a compound having a solubility parameter of greater than 26 $(MPa)^{1/2}$ as measured by the Fedors method. The solubility parameter (SP) is a value at such a temperature (25° C.) that an oxygen atom (—O—) constituting an ester bond has an energy of vaporization of 3350 J/mol and a molar volume of 3.8 $cm^3/mol$.

(15) In the oxide production method according to any one of (1) to (14), the imide compound may be a compound selected from the group consisting of N-hydroxysuccinimide, N-hydroxyphthalimide, N,N'-dihydroxypyromellitic diimide, N-hydroxyglutarimide, N-hydroxy-1,8-naphthalenedicarboximide, N,N'-dihydroxy-1,8;4,5-naphthalenetetracarboxylic diimide, and compounds each obtained by introducing a protecting group to hydroxy of these compounds.

(16) A method for oxidizing a substrate. The method includes oxidizing a substrate (A) in the presence of oxygen and ozone under catalysis of an imide compound containing a cyclic imide skeleton represented by Formula (I). The substrate (A) is a compound selected from the group consisting of (A1) compounds containing a heteroatom and a carbon-hydrogen bond at an adjacent position to the heteroatom, (A2) compounds containing a carbon-heteroatom double bond, (A3) compounds containing a methine carbon atom, (A4) compounds containing an unsaturated bond and a carbon-hydrogen bond at an adjacent position to the unsaturated bond, (A5) alicyclic compounds, (A6) conjugated compounds, (A7) amine compounds, (A8) aromatic compounds, (A9) normal alkanes, and (A10) olefins.

Advantageous Effects of Invention

With the oxide production method according to the present invention, a corresponding oxide can be produced in a high yield under mild conditions even when a commercially available imide compound is used as intact as a catalyst, even when normal alkanes, which are resistant to oxidation, are used as the substrate, and/or even when the oxidation is performed approximately in the absence of solvents.

With the substrate oxidation method according to the present invention, a substrate can be oxidized with high conversion under mild conditions even when a commercially available imide compound is used as intact as a catalyst, even when normal alkanes, which are resistant to oxidation, are used as the substrate, and/or even when the oxidation is performed approximately in the absence of solvents.

These configurations allow the present invention to be applicable typically to fuel reforming by promoting oxidation of hydrocarbons, sulfides, inorganic components, and any other components in fuels such as gasoline; oxygen gas purification via oxidation of carbon monoxide in the oxygen gas; oxidative removal of hydrocarbons from silicon oxides; removal of nitrogen oxides from Diesel engines; and exhaust gas purification via oxidative removal of hydrocarbons and carbon monoxide in the exhaust gas.

DESCRIPTION OF EMBODIMENTS

Catalyst

Figure 1:
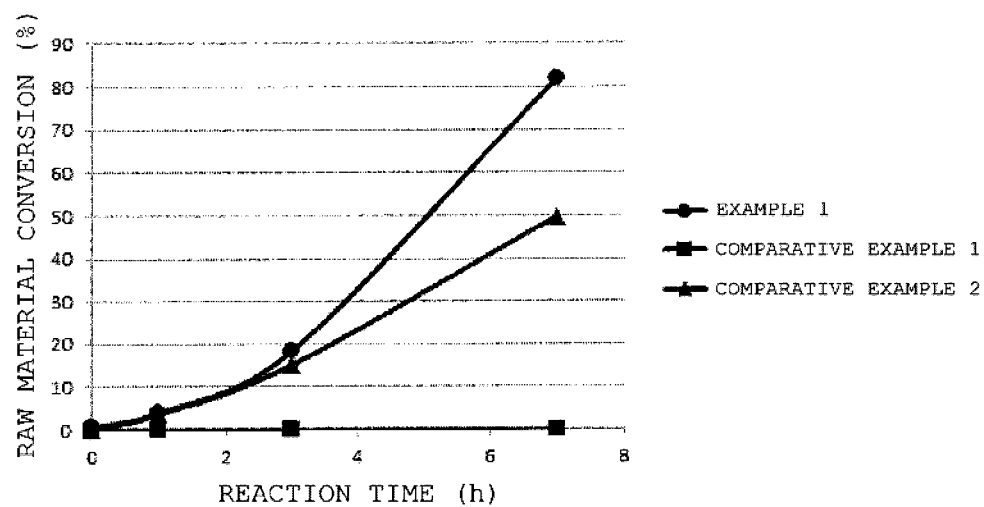
FIG. 1 is a graph illustrating how a raw material conversion varies depending on a reaction time in oxidation reactions according to Example 1 and Comparative Examples 1 and 2.

The present invention uses, as a catalyst, the imide compound containing a cyclic imide skeleton represented by Formula (I).

In Formula (I), the bond between the specified nitrogen atom and X is a single bond or double bond. The imide compound may contain two or more cyclic imide skeletons represented by Formula (I) per molecule. Assume that X is an —OR group, and R is a hydroxy-protecting group. In this case, the imide compound may contain two or more of a moiety (N-oxy cyclic imide skeleton) corresponding to the cyclic imide skeleton excluding R, where the N-oxy cyclic imide skeletons are bonded with each other via R.

Examples of the hydroxy-protecting group as R include, but are not limited to, alkyl (e.g., $C_1$-$C_4$ alkyl such as methyl and t-butyl), alkenyl (e.g., allyl), cycloalkyl (e.g., cyclohexyl), aryl (e.g., 2,4-dinitrophenyl), aralkyl (e.g., benzyl, 2,6-dichlorobenzyl, 3-bromobenzyl, 2-nitrobenzyl, and triphenylmethyl); groups that can form an acetal or hemiacetal with hydroxy, such as substituted methyl (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl), substituted ethyl (e.g., 1-ethoxyethyl, 1-methyl-1-methoxyethyl, 1-isopropoxyethyl, 2,2,2-trichloroethyl, and 2-methoxyethyl), tetrahydropyranyl, tetrahydrofuranyl, and 1-hydroxyalkyl (e.g., 1-hydroxyethyl, 1-hydroxyhexyl, 1-hydroxydecyl, 1-hydroxyhexadecyl, and 1-hydroxy-1-phenylmethyl); acyl (e.g., aliphatic saturated or unsaturated acyl including $C_1$-$C_{20}$ aliphatic acyl such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl; acetoacetyl; alicyclic acyl including cycloalkanecarbonyl such as cyclopentanecarbonyl and cyclohexanecarbonyl; and aromatic acyl such as benzoyl and naphthoyl); as well as sulfonyl (e.g., methanesulfonyl, ethanesulfonyl, trifluoromethanesulfonyl, benzenesulfonyl, p-toluenesulfonyl, and naphthalenesulfonyl), alkoxycarbonyl (e.g., $C_1$-$C_4$ alkoxy-carbonyl such as methoxycarbonyl, ethoxycarbonyl, and t-butoxycarbonyl), aralkyloxycarbonyl (e.g., benzyloxycarbonyl and p-methoxybenzyloxycarbonyl), substituted or unsubstituted carbamoyl (e.g., carbamoyl, methylcarbamoyl, and phenylcarbamoyl), groups corresponding to inorganic acids (e.g., sulfuric acid, nitric acid, phosphoric acid, and boric acid), except for removing a OH group therefrom, dialkylphosphinothioyl (e.g., dimethylphosphinothioyl), diarylphosphinothioyl (e.g., diphenylphosphinothioyl), and substituted silyl (e.g., trimethylsilyl, t-butyldimethylsilyl, tribenzylsilyl, and triphenylsilyl).

Assume that X is an —OR group, and two or more of the moiety (N-oxy cyclic imide skeleton) of the cyclic imide skeleton excluding R are bonded with each other via R. Examples of R in this case include, but are not limited to, multivalent hydrocarbon groups (in particular, groups that form an acetal with two hydroxy groups), including polycarboxylic acid acyl such as oxalyl, malonyl, succinyl, glutaryl, adipoyl, phthaloyl, isophthaloyl, and terephthaloyl; carbonyl; and methylene, ethylidene, isopropylidene, cyclopentylidene, cyclohexylidene, and benzylidene.

Preferred examples of R include, but are not limited to, hydrogen; groups that can form an acetal or hemiacetal with hydroxy; acyl, sulfonyl, alkoxycarbonyl, carbamoyl, and other groups corresponding to acids, except for removing a OH group therefrom, and other hydrolyzable protecting groups that can leave via hydrolysis. The acids are exemplified by, but are not limited to, carboxylic acid, sulfonic acid, carbonic acid, carbamic acid, sulfuric acid, phosphoric acid, and boric acid.

In Formula (I), n is selected from 0 and 1. Specifically, Formula (I) represents a five-membered cyclic imide skeleton when n is 0; and represents a six-membered cyclic imide skeleton when n is 1.

Examples of representative imide compound include, but are not limited to, imide compounds represented by Formula (1) below. In Formula (1), n is selected from 0 and 1; X is selected from an oxygen atom and an —OR group, where R is selected from hydrogen and a hydroxy-protecting group; and $R^1$, $R^2$, $R^3$, $R^4$, $R^5$, and $R^6$ are each, identically or differently, selected from hydrogen, halogen, alkyl, aryl, cycloalkyl, hydroxy, alkoxy, carboxy, substituted oxycarbonyl, acyl, and acyloxy. At least two of $R^1$, $R^2$, $R^3$, $R^4$, $R^5$, and $R^6$ may be linked to each other to form a double bond, or may form a ring with a carbon atom constituting the cyclic imide skeleton. One or more of the cyclic imide group specified in Formula (1) may be bonded to at least one of $R^1$, $R^2$, $R^3$, $R^4$, $R^5$, and $R^6$, to the double bond formed by at least two of $R^1$, $R^2$, $R^3$, $R^4$, $R^5$, and $R^6$ linked to each other, and/or to the ring formed by at least two of $R^1$, $R^2$, $R^3$, $R^4$, $R^5$, and $R^6$ with a carbon atom constituting the cyclic imide skeleton. Formula (1) is expressed as follows:

[Chem. 3]

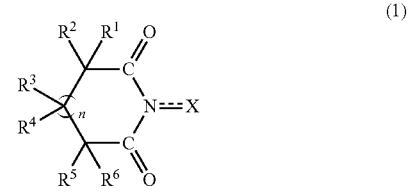

(1)

As the substituents $R^1$, $R^2$, $R^3$, $R^4$, $R^5$, and $R^6$ in the imide compounds represented by Formula (1), examples of the halogen include but are not limited to, iodine, bromine, chlorine, and fluorine. Examples of the alkyl include, but are not limited to, straight chain or branched chain alkyl containing 1 to about 30 carbon atoms (in particular 1 to 20 carbon atoms), such as methyl, ethyl, propyl, isopropyl, butyl, isobutyl, s-butyl, t-butyl, hexyl, decyl, dodecyl, tetradecyl, and hexadecyl.

Examples of the aryl include, but are not limited to, phenyl and naphthyl. Examples of the cycloalkyl include, but are not limited to, cyclopentyl and cyclohexyl. Examples of the alkoxy include, but are not limited to, alkoxy containing 1 to about 30 carbon atoms (in particular, 1 to 20 carbon atoms), such as methoxy, ethoxy, isopropoxy, butoxy, t-butoxy, hexyloxy, octyloxy, decyloxy, dodecyloxy, tetradecyloxy, and octadecyloxy.

Examples of the substituted oxycarbonyl include, but are not limited to, $C_1$-$C_{30}$ alkoxy-carbonyl such as methoxycarbonyl, ethoxycarbonyl, isopropoxycarbonyl, butoxycarbonyl, t-butoxycarbonyl, hexyloxycarbonyl, decyloxycarbonyl, and hexadecyloxycarbonyl, of which $C_1$-$C_{20}$ alkoxy-carbonyl is typified; cycloalkyloxycarbonyl such as cyclopentyloxycarbonyl and cyclohexyloxycarbonyl, of which 3- to 20-membered cycloalkyloxy-carbonyl is typified; aryloxycarbonyl such as phenyloxycarbonyl and naphthyloxycarbonyl, of which $C_6$-$C_{20}$ aryloxy-carbonyl is typified; and aralkyloxycarbonyl such as benzyloxycarbonyl, of which $C_7$-$C_{21}$ aralkyloxy-carbonyl is typified.

Examples of the acyl include, but are not limited to, aliphatic saturated or unsaturated acyl including $C_1$-$C_{30}$ aliphatic acyl such as formyl, acetyl, propionyl, butyryl, isobutyryl, valeryl, pivaloyl, hexanoyl, octanoyl, decanoyl, lauroyl, myristoyl, palmitoyl, and stearoyl, of which $C_1$-$C_{20}$ aliphatic acyl is typified; acetoacetyl; alicyclic acyl including cycloalkanecarbonyl such as cyclopentanecarbonyl and cyclohexanecarbonyl; and aromatic acyl such as benzoyl and naphthoyl.

Examples of the acyloxy include, but are not limited to, aliphatic saturated or unsaturated acyloxy including $C_1$-$C_{30}$ aliphatic acyloxy such as formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, and stearoyloxy, of which $C_1$-$C_{20}$ aliphatic acyloxy is typified; acetoacetyloxy; alicyclic acyloxy including cycloalkanecarbonyloxy such as cyclopentanecarbonyloxy and cyclohexanecarbonyloxy; and aromatic acyloxy such as benzoyloxy and naphthoyloxy.

At least two of the substituents $R^1$, $R^2$, $R^3$, $R^4$, $R^5$, and $R^6$ may be linked to each other to form a ring with a carbon atom constituting the cyclic imide skeleton. The ring is exemplified by, but is not limited to, 5- to 12-membered rings, of which 6- to 10-membered rings are particularly preferred. The rings include hydrocarbon rings, heterocyclic rings, and fused heterocyclic rings. Examples of such rings include, but are not limited to, non-aromatic alicyclic rings including optionally substituted cycloalkane rings such as cyclohexane ring, and optionally substituted cycloalkene rings such as cyclohexene ring; non-aromatic bridged rings including optionally substituted bridged hydrocarbon rings such as 5-norbornene ring; and optionally substituted aromatic rings (including fused rings), such as benzene ring and naphthalene ring. Examples of the substituents which the rings may have include, but are not limited to, alkyl, haloalkyl, hydroxy, alkoxy, carboxy, substituted oxycarbonyl, acyl, acyloxy, nitro, cyano, amino, and halogen.

One or more of the cyclic imide group specified in Formula (1) may be bonded to any of $R^1$, $R^2$, $R^3$, $R^4$, $R^5$, and $R^6$, and/or to the double bond formed by at least two of $R^1$, $R^2$, $R^3$, $R^4$, $R^5$, and $R^6$ linked to each other, and/or to the ring formed by a carbon atom constituting the cyclic imide skeleton together with at least two of $R^1$, $R^2$, $R^3$, $R^4$, $R^5$, and $R^6$ linked to each other. For example, assume that one of $R^1$, $R^2$, $R^3$, $R^4$, $R^5$, and $R^6$ is alkyl containing two or more carbon atoms. In this case, the cyclic imide group may be formed as including adjacent two carbon atoms constituting the alkyl. Assume that at least two of $R^1$, $R^2$, $R^3$, $R^4$, $R^5$, and $R^6$ are linked to each other to form a double bond. In this case, the cyclic imide group may be formed as including the double bond. At least two of $R^1$, $R^2$, $R^3$, $R^4$, $R^5$, and $R^6$ may be linked to each other to form the cyclic imide group with a carbon atom constituting the cyclic imide skeleton.

Preferred examples of the imide compound include compounds represented by formulae below. In the formulae, $R^{11}$ to $R^{16}$ are each, identically or differently, selected from hydrogen, halogen, alkyl, aryl, cycloalkyl, hydroxy, alkoxy, carboxy, substituted oxycarbonyl, acyl, and acyloxy. $R^{17}$ to $R^{26}$ are each, identically or differently, selected from hydrogen, alkyl, haloalkyl, hydroxy, alkoxy, carboxy, substituted oxycarbonyl, acyl, acyloxy, nitro, cyano, amino, and halogen. Adjacent groups of $R^{17}$ to $R^{26}$ may be linked to form the five-membered or six-membered cyclic imide skeleton specified in any of Formulae (1c), (1d), (1e), (1f), (1h), and (1i). "A" is selected from methylene and oxygen. X is as defined above.

[Chem. 4]

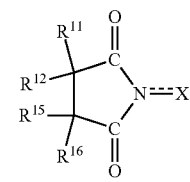

(1a)

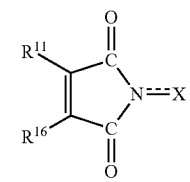

(1b)

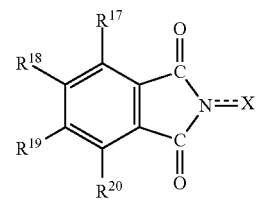

(1c)

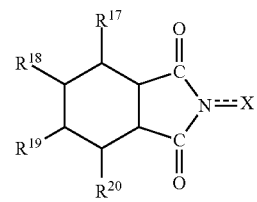

(1d)

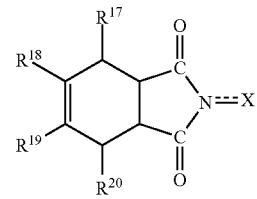

(1e)

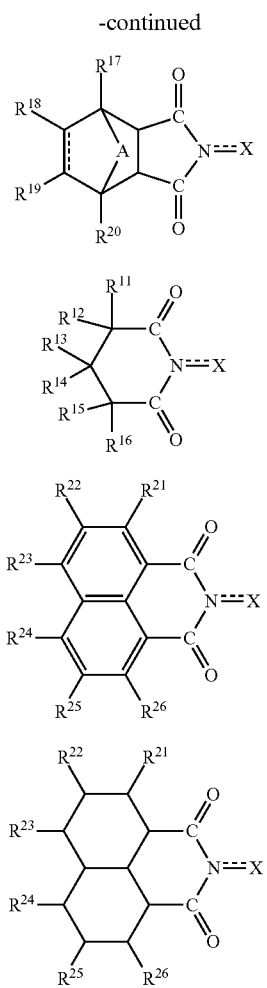

The halogen, alkyl, aryl, cycloalkyl, hydroxy, alkoxy, carboxy, substituted oxycarbonyl, acyl, and acyloxy as the substituents $R^{11}$ to $R^{16}$ are exemplified as with the corresponding groups as $R^1$ to $R^6$.

Examples of the substituents $R^{17}$ to $R^{26}$ are as follows. Examples of the alkyl include, but are not limited to, alkyl as exemplified above, of which alkyl containing 1 to about 6 carbon atoms is preferred, and lower alkyl containing 1 to 4 carbon atoms is particularly preferred. Examples of the haloalkyl include, but are not limited to, haloalkyl containing 1 to about 4 carbon atoms, such as trifluoromethyl. Examples of the alkoxy include alkoxy as exemplified above, of which lower alkoxy containing 1 to about 4 carbon atoms is preferred. Examples of the substituted oxycarbonyl include, but are not limited to, substituted oxycarbonyl as exemplified above, such as alkoxycarbonyl, cycloalkyloxycarbonyl, aryloxycarbonyl, and aralkyloxycarbonyl. Examples of the acyl include acyl as exemplified above, such as aliphatic saturated or unsaturated acyl, acetoacetyl, alicyclic acyl, and aromatic acyl. Examples of the acyloxy include the acyloxy as exemplified above, such as aliphatic saturated or unsaturated acyloxy, acetoacetyloxy, alicyclic acyloxy, and aromatic acyloxy. Examples of the halogen include, but are not limited to, fluorine, chlorine, and bromine. Among them, the substituents $R^{17}$ to $R^{26}$ are each preferably selected from hydrogen, lower alkyl containing 1 to about 4 carbon atoms, carboxy, substituted oxycarbonyl, nitro, and halogen.

The present invention uses oxygen as an oxidizer in the coexistence of ozone. This configuration allows oxidation of the substrate (A) with very excellent oxidizing power. This allows the reaction to proceed rapidly in the absence of solvents and to give an oxide efficiently, even when the imide compound has a solubility parameter as estimated by the Fedors method of typically greater than 26 $(MPa)^{1/2}$ (preferably from greater than 26 $(MPa)^{1/2}$ to 40 $(MPa)^{1/2}$). The solubility parameter (SP) is a value at a temperature (25° C.) at which an oxygen atom (—O—) constituting an ester bond has an energy of vaporization of 3350 J/mol and a molar volume of 3.8 cm$^3$/mol. The solubility parameter SP may be determined by methods described in literature (see, for example, R. F. Fedors, Polym. Eng. Sci., 14(2), 147 (1974); E. A. Grulke, Polymer Handbook, VII/675; Yuji HARAZAKI, Paint Technology, 3, 129(1987).

Of the preferred imide compounds, representative examples of compounds containing a five-membered cyclic imide skeleton include, but are not limited to, compounds of Formula (1) in which X is an —OR group and R is hydrogen, such as N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, HET acid N-hydroxyimide (N-hydroxy-1,4,5,6,7,7-hexachlorobicyclo[2.2.1]hept-5-ene-2,3-dicarboximide), himic acid N-hydroxyimide (N-hydroxy-bicyclo[2.2.1]hept-5-ene-2,3-dicarboximide), N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, and N-hydroxy-4,5-bis(phenoxycarbonyl)phthalimide; compounds corresponding to these compounds, except that R is acyl such as acetyl, propionyl, or benzoyl; compounds of Formula (1) in which X is an —OR group and R is a group capable of forming an acetal or hemiacetal with hydroxy, such as N-methoxymethyloxyphthalimide, N-(2-methoxyethoxymethyloxy)phthalimide, and N-tetrahydropyranyloxyphthalimide; compounds of Formula (1) in which X is an —OR group and R is sulfonyl, such as N-methanesulfonyloxyphthalimide and N-(p-toluenesulfonyloxy)phthalimide; and compounds of Formula (1) in which X is an —OR group and R is a group corresponding to an inorganic acid, except for removing a OH group from the acid, such as sulfuric ester, nitric ester, phosphoric ester, and boric acid ester of N-hydroxyphthalimide.

Of the preferred imide compounds, typical examples of compounds containing a six-membered cyclic imide skeleton include, but are not limited to, compounds of Formula (1) in which X is an —OR group and R is hydrogen, such as N-hydroxyglutarimide, N-hydroxy-α,α-dimethylglutarimide, N-hydroxy-β,β-dimethylglutarimide, N-hydroxy-1,8-decahydronaphthalenedicarboximide, N,N'-dihydroxy-1, 8;4,5-decahydronaphthalenetetracarboxylic diimide, N-hydroxy-1,8-naphthalenedicarboximide (N-hydroxynaphthalimide), and N,N'-dihydroxy-1,8;4,5-naphthalenetetracarboxylic diimide; compounds corresponding to these compounds, except that R is acyl such as acetyl, propionyl, or benzoyl; compounds of Formula (1) in which X is an —OR group and R is a group capable of forming an acetal or hemiacetal with hydroxy, such as N-methoxymethyloxy-1,8-naphthalenedicarboximide and N,N'-bis(methoxymethyloxy)-1,8;4,5-naphthalenetetracarboxylic diimide; compounds of Formula (1) in which X is an —OR group and R is sulfonyl, such as N-methanesulfonyloxy-1,8-naphthalenedicarboximide and N,N'-bis(methanesulfonyloxy)-1,8;4,5-naphthalenetetracarboxylic diimide; and compounds of Formula (1) in which X is an —OR group and R is a group corresponding to an inorganic acid, except for removing a OH group therefrom, such as sulfuric esters, nitric esters, phosphoric esters, and boric acid esters of N-hydroxy-1,8-naphthalenedicarboximide and N,N'-dihydroxy-1,8;4,5-naphthalenetetracarboxylic diimide.

Of the imide compounds, N-hydroxyimide compounds, i.e., compounds in which X is an —OR group and R is hydrogen, may be produced via any common imidization reaction. For example, these compounds may be produced by a process of imidizing a corresponding acid anhydride via a reaction with hydroxylamine through ring opening of the acid anhydride group and ring closing. Of the imide compounds, compounds in which X is an —OR group and R is a hydroxy-protecting group may be produced by introducing a desired protecting group into a corresponding N-hydroxyimide compound, i.e., a corresponding compound in which R is hydrogen, using a common protecting group introducing reaction. For example, N-acetoxyphthalimide may be produced typically by allowing N-hydroxyphthalimide to react with acetic anhydride, or by allowing N-hydroxyphthalimide to react with an acetyl halide in the presence of a base.

Particularly preferred examples of the imide compound include, but are not limited to, N-hydroxyimide compounds derived from aliphatic polycarboxylic anhydrides or aromatic polycarboxylic anhydrides, such as N-hydroxysuccinimide (SP: 33.5 $(MPa)^{1/2}$), N-hydroxyphthalimide (SP: 33.4 $(MPa)^{1/2}$), N,N'-dihydroxypyromellitic diimide, N-hydroxyglutarimide, N-hydroxy-1,8-naphthalenedicarboximide, and N,N'-dihydroxy-1,8;4,5-naphthalenetetracarboxylic diimide; and compounds obtained by introducing a protecting group into hydroxy of the N-hydroxyimide compounds.

Each of different imide compounds may be used alone or in combination as the imide compound. The imide compound may be formed within the reaction system. According to the present invention, however, any of commercial products may be appropriately used. Examples of the commercial products include, but are not limited to, trade name N-Hydroxyphthalimide (supplied by Wako Pure Chemical Industries, Ltd.) and trade name N-Hydroxysuccinimide (supplied by Wako Pure Chemical Industries, Ltd.).

The imide compound may be used as being supported on a support. Examples of the support include, but are not limited to, porous supports such as activated carbon, zeolite, silica, silica-alumina, and bentonite.

The imide compound may be used in an amount of typically about 0.0000001 to about 1 mole, preferably 0.00001 to 0.5 mole, particularly preferably 0.0001 to 0.4 mole, and most preferably 0.05 to 0.4 mole, per mole of the substrate (A). The imide compound, when used in an amount within the range, allows the oxidation reaction to proceed at an excellent reaction rate.

Promoter

In the present invention, a metallic compound is preferably used as a promoter in combination with the imide compound used as the catalyst. The combination use of the catalyst and the metallic compound may contribute to a still higher reaction rate.

Examples of a metal element constituting the metallic compound include, but are not limited to, cobalt, manganese, zirconium, and molybdenum. The metal element may have a valence not limited, but typically from zero- to hexa-valence.

Examples of the metallic compound include, but are not limited to, inorganic compounds including, of the metal elements, the metal elements themselves (elementary metals), as well as hydroxides, oxides (including complex oxides), halides (fluorides, chlorides, bromides, and iodides), oxoacid salts (e.g., nitrates, sulfates, phosphates, borates, and carbonates), isopolyacid salts, and heteropolyacid salts; and organic compounds including, of the metal elements, organic acid salts (e.g., acetates, propionates, cyanides, naphthenates, and stearate), and complexes.

Examples of ligands constituting the complexes include, but are not limited to, OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphorus compounds including phosphines (e.g., triarylphosphines such as triphenylphosphine), and nitrogen-containing compounds such as $NH_3$ (ammine), NO, $NO_2$ (nitro), $NO_3$ (nitrato), ethylenediamine, diethylenetriamine, pyridine, and phenanthroline.

By taking cobalt compounds as examples, the metallic compound are exemplified by, but are not limited to, divalent or trivalent cobalt compounds including inorganic compounds such as cobalt hydroxide, cobalt oxide, cobalt chloride, cobalt bromide, cobalt nitrate, cobalt sulfate, and cobalt phosphate; organic acid salts such as cobalt acetate, cobalt naphthenate, and cobalt stearate; and complexes such as cobalt acetylacetonates. Non-limiting examples of compounds of other metal elements include compounds corresponding to the cobalt compounds. Each of different metallic compounds may be used alone or in combination. For a significantly higher reaction rate, the use of at least a cobalt compound is preferred, and the combination use of a cobalt compound and a manganese compound is particularly preferred in the present invention.

The metallic compound may be used in an amount of typically about 0.001 to about 10 moles, preferably 0.005 to 3 moles, and particularly preferably 0.01 to 1 mole, per mole of the imide compound. When the metallic compound includes two or more different metallic compounds, the term "amount" refers to the total amount of the two or more metallic compounds. The metallic compound may also be used in an amount of typically about 0.00001 to about 10 mole percent, and preferably 0.2 to 2 mole percent, relative to the substrate (A).

The metallic compound may be added at once upon charging of materials, or may be added continuously or intermittently to the reaction system. For a higher reaction rate, the metallic compound in the present invention is preferably added continuously or intermittently. The metallic compound (in particular, the cobalt compound) is most preferably added intermittently in an amount of typically 0.005 to 0.500 mole, and preferably 0.100 to 0.300 mole, per mole of the imide compound.

Solvent

In the present invention, a small amount (e.g., about 0.1 to about 10 times the catalyst weight) of a solvent may be used so as to dissolve the catalyst. However, the present invention uses oxygen as an oxidizer in the coexistence of ozone, and this configuration allows the oxidation reaction to proceed even when approximately no solvent is used. Accordingly, the solvent may be used typically in such an amount that the total amount of the substrate (A) and the oxide of the substrate (A) is about 70 percent by weight or more, preferably 85 percent by weight or more, and particularly preferably 95 percent by weight or more, relative to the total amount of liquid components in the reaction system. Assume that approximately no solvent is used. This configuration may eliminate the need for separating the oxide, a reaction product, from the solvent and may contribute to simplification of the production process.

Examples of the solvent include, but are not limited to, organic acids such as acetic acid and propionic acid; nitriles such as acetonitrile, propionitrile, and benzonitrile; amides such as formamide, acetamide, dimethylformamide, and dimethylacetamide; aliphatic hydrocarbons such as hexane and octane; halogenated hydrocarbons such as chloroform, dichloromethane, dichloroethane, carbon tetrachloride, chlorobenzene, and trifluoromethylbenzene; nitro compounds such as nitrobenzene, nitromethane, and nitroethane; esters such as ethyl acetate and butyl acetate; and mixtures of these solvents.

Oxidizer

The present invention uses oxygen as an oxidizer in the coexistence of ozone. The combination use of oxygen as the oxidizer with ozone can promote the abstracting of hydrogen from the substrate (A) and can activate radical reactions. This configuration can promote the oxidation reaction even under mild conditions. Under such mild conditions, the reaction pressure may be normal atmospheric pressure, and the reaction temperature may be typically from room temperature to about 200° C., preferably 50° C. to 130° C., and particularly preferably 60° C. to 100° C. Assume that the reaction is performed under flow of oxygen gas and ozone gas. In this case, the mixture of the oxygen gas and the ozone gas may contain the ozone gas in an amount of typically about 0.1 to about 10 percent by volume relative to the oxygen gas, from the viewpoints of reactivity and economic efficiency.

The oxygen is preferably molecular oxygen. Examples of the molecular oxygen include pure oxygen; oxygen diluted with an inert gas such as nitrogen, helium, argon, and/or carbon dioxide; and air under normal atmospheric pressure or under pressure (e.g., at 1 to 100 atmospheres). The molecular oxygen may be used in an amount not limited, as long as being 1 mole or more per mole of the substrate (A).

The ozone acts as a radical generator (radical precursor) in the present invention. The ozone for use herein is preferably ozone gas. The ozone gas may be used in an amount not limited, as long as being 0.01 mole or more per mole of the substrate (A). The ozone gas may be fed intermittently or continuously, as long as the reaction proceeds smoothly. Another radical generator such as azobisisobutyronitrile (AIBN) may be used in combination with ozone.

According to the present invention, the reaction is performed in the presence of oxygen and ozone, or under flow of oxygen gas and ozone gas. Examples of the way to allow the gases (oxygen gas and ozone gas) to flow include a method of allowing the gases to flow through a gas phase in the reaction system; and a method of allowing the gases to flow through a liquid phase in the reaction system. The gases may flow at a flow rate (circulation speed) of typically about 1 to about 40 L/min., and preferably 10 to 30 L/min., per mole of the substrate (A).

A larger contact area and/or a longer contact time between the gases and the substrate is preferred in the present invention for a still higher reaction rate. For example, the reaction is preferably performed with bubbling of the oxygen gas and the ozone gas.

Substrate (A)

An organic compound for use as the reaction substrate (A) in the present invention is preferably selected from compounds that can form a stable radical, such as at least one compound selected from the group consisting of (A1) compounds containing a heteroatom and a carbon-hydrogen bond at an adjacent position to the heteroatom, (A2) compounds containing a carbon-heteroatom double bond, (A3) compounds containing a methine carbon atom, (A4) compounds containing an unsaturated bond and a carbon-hydrogen bond at an adjacent position to the unsaturated bond, (A5) alicyclic compounds, (A6) conjugated compounds, (A7) amine compounds, (A8) aromatic compounds, (A9) normal alkanes, and (A10) olefins.

These compounds may each have one or more substituents within ranges not adversely affecting the reaction. Examples of the substituents include, but are not limited to, halogen, hydroxy, mercapto, oxo, substituted oxy (e.g., alkoxy, aryloxy, and acyloxy), substituted thio, carboxy, substituted oxycarbonyl, substituted or unsubstituted carbamoyl, cyano, nitro, substituted or unsubstituted amino, sulfo, alkyl, alkenyl, alkynyl, alicyclic hydrocarbon groups, aromatic hydrocarbon groups, and heterocyclic groups.

Examples of the compounds (A1) containing a heteroatom and a carbon-hydrogen bond at an adjacent position to the heteroatom include, but are not limited to, (A1-1) primary or secondary alcohols, and primary or secondary thiols; (A1-2) ethers containing a carbon-hydrogen bond at an adjacent position to oxygen, and sulfides containing a carbon-hydrogen bond at an adjacent position to sulfur; and (A1-3) acetals (including hemiacetals) containing a carbon-hydrogen bond at an adjacent position to oxygen, and thioacetals (including thiohemiacetals) containing a carbon-hydrogen bond at an adjacent position to sulfur.

The primary or secondary alcohols in the category (A1-1) include a wide variety of alcohols. The alcohols may be any of monohydric, dihydric, and polyhydric alcohols.

Examples of representative primary alcohols include, but are not limited to, saturated or unsaturated aliphatic primary alcohols containing 1 to about 30 (preferably 1 to 20, and particularly preferably 1 to 15) carbon atoms, such as methanol, ethanol, 1-propanol, 1-butanol, 1-pentanol, 1-hexanol, 1-octanol, 1-decanol, 2-buten-1-ol, ethylene glycol, trimethylene glycol, hexamethylene glycol, and pentaerythritol; saturated or unsaturated alicyclic primary alcohols such as cyclopentylmethyl alcohol, cyclohexylmethyl alcohol, and 2-cyclohexylethyl alcohol; aromatic primary alcohols such as benzyl alcohol, 2-phenylethyl alcohol, 3-phenylpropyl alcohol, and cinnamic alcohol; and heterocyclic alcohols such as 2-hydroxymethylpyridine.

Examples of representative secondary alcohols include, but are not limited to, saturated or unsaturated aliphatic secondary alcohols containing 3 to about 30 (preferably 3 to 20, and particularly preferably 3 to 15) carbon atoms, such as 2-propanol, s-butyl alcohol, 2-pentanol, 2-octanol, 2-penten-4-ol, 1,2-propanediol, and 2,3-butanediol, as well as vicinal diols such as 2,3-pentanediol; secondary alcohols containing an aliphatic hydrocarbon group and an alicyclic hydrocarbon (e.g., cycloalkyl) both bonded to the carbon atom to which hydroxy is bonded, such as 1-cyclopentylethanol and 1-cyclohexylethanol; saturated or unsaturated alicyclic secondary alcohols (including bridged secondary alcohols) containing 3 to about 20 members (preferably 3 to 15 members, particularly preferably 5 to 15 members, and most preferably 5 to 8 members), such as cyclopentanol, cyclohexanol, cyclooctanol, cyclododecanol, 2-cyclohexen-1-ol, 2-adamantanol, 2-adamantanols containing one to four hydroxy groups at a bridgehead position(s), and 2-adamantanols containing an oxo group(s) on the adamantane ring; aromatic secondary alcohols such as 1-phenylethanol; and heterocyclic secondary alcohols such as 1-(2-pyridyl)ethanol.

Representative examples of the alcohols also include alcohols containing a bridged hydrocarbon group (compounds containing a bridged hydrocarbon group bonded to a carbon atom to which hydroxy is bonded), such as 1-adamantanemethanol, α-methyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4a-decahydronaphthalenemethanol, α-methyl-4a-perhydrofluorenemethanol, α-methyl-2-tricyclo[5.2.1.0$^{2,6}$]decanemethanol, and α-methyl-1-norbornanemethanol.

Examples of the primary or secondary thiols in the category (A1-1) include, but are not limited to, thiols corresponding to the primary or secondary alcohols.

Examples of the ethers containing a carbon-hydrogen bond at an adjacent position to oxygen in the category (A1-2) include, but are not limited to, aliphatic ethers such as dimethyl ether, diethyl ether, dipropyl ether, diisopropyl ether, dibutyl ether, and diallyl ether; aromatic ethers such as anisole, phenetole, dibenzyl ether, and phenyl benzyl ether; and cyclic ethers (to which an aromatic ring and/or a non-aromatic ring may be fused), such as dihydrofuran, tetrahydrofuran, pyran, dihydropyran, tetrahydropyran, morpholine, chroman, and isochroman.

Examples of the sulfides containing a carbon-hydrogen bond at an adjacent position to sulfur in the category (A1-2) include, but are not limited to, sulfides corresponding to the ethers containing a carbon-hydrogen bond at an adjacent position to oxygen.

Examples of the acetals containing a carbon-hydrogen bond at an adjacent position to oxygen in the category (A1-3) include acetals derived typically from aldehydes with alcohols or acid anhydrides. The acetals include cyclic acetals and acyclic acetals. Examples of the aldehydes include, but are not limited to, aliphatic aldehydes such as formaldehyde, acetaldehyde, propionaldehyde, butyraldehyde, and isobutyraldehyde; alicyclic aldehydes such as cyclopentanecarbaldehyde and cyclohexanecarbaldehyde; and aromatic aldehydes such as benzaldehyde and phenylacetaldehyde. Examples of the alcohols include, but are not limited to, monohydric alcohols such as methanol, ethanol, 1-propanol, 1-butanol, and benzyl alcohol; and dihydric alcohols such as ethylene glycol, propylene glycol, 1,3-propanediol, and 2,2-dibromo-1,3-propanediol. Representative examples of the acetals include, but are not limited to, 1,3-dioxolane compounds such as 1,3-dioxolane, 2-methyl-1,3-dioxolane, and 2-ethyl-1,3-dioxolane; 1,3-dioxane compounds such as 2-methyl-1,3-dioxane; and dialkylacetal compounds such as acetaldehyde dimethyl acetal.

Examples of the thioacetals containing a carbon-hydrogen bond at an adjacent position to sulfur in the category (A1-3) include thioacetals corresponding to the acetals containing a carbon-hydrogen bond at an adjacent position to oxygen.

Examples of the compounds (A2) containing a carbon-heteroatom double bond include, but are not limited to, (A2-1) carbonyl-containing compounds, (A2-2) thiocarbonyl-containing compounds, and (A2-3) imines. The carbonyl-containing compounds (A2-1) include ketones and aldehydes and are exemplified by, but not limited to, chain ketones such as acetone, methyl ethyl ketone, methyl isobutyl ketone, 3-pentanone, methyl vinyl ketone, methyl cyclohexyl ketone, and acetophenone; cyclic ketones such as cyclopentanone, cyclohexanone, 4-methylcyclohexanone, isophorone, cyclodecanone, cyclododecanone, 1,4-cyclooctanedione, 2,2-bis(4-oxocyclohexyl)propane, and 2-adamantanone; 1,2-dicarbonyl compounds (e.g., α-diketones), such as biacetyl (2,3-butanedione), bibenzoyl (i.e., benzil), acetylbenzoyl, and cyclohexane-1,2-dione; α-keto-alcohols such as acetoin and benzoin; aliphatic aldehydes such as acetaldehyde, propionaldehyde, butanal, hexanal, succinaldehyde, glutaraldehyde, and adipaldehyde; alicyclic aldehydes such as cyclohexancarbaldehyde, citral, and citronellal; aromatic aldehydes such as benzaldehyde, carboxybenzaldehyde, nitrobenzaldehyde, cinnamaldehyde, salicylaldehyde, anisaldehyde, phthalaldehyde, isophthalaldehyde, and terephthalaldehyde; and heterocyclic aldehydes such as furfural and nicotinaldehyde.

Examples of the thiocarbonyl-containing compounds (A2-2) include, but are not limited to, thiocarbonyl-containing compounds corresponding to the carbonyl-containing compounds (A2-1).

Examples of the imines (A2-3) include, but are not limited to, imines (also including oximes and hydrazones) derived from the carbonyl-containing compounds (A2-1) with ammonia or amines. Examples of the amines include amines such as methylamine, ethylamine, propylamine, butylamine, hexylamine, benzylamine, cyclohexylamine, and aniline; hydroxyamines such as hydroxylamine and O-methylhydroxyamine; and hydrazines such as hydrazine, methylhydrazine, and phenylhydrazine.

The compounds (A3) containing a methine carbon atom include, but are not limited to, (A3-1) cyclic compounds containing a methine group (namely, a methine carbon-hydrogen bond) as a ring-constitutional unit; and (A3-2) chain compounds containing a methine carbon atom.

The cyclic compounds (A3-1) include, but are not limited to, (A3-1a) bridged compounds containing at least one methine group; and (A3-1b) non-aromatic cyclic compounds (e.g., alicyclic hydrocarbons) containing a ring and a hydrocarbon group bonded to the ring. The bridged compounds also include compounds containing two rings which share two carbon atoms (e.g., hydrogenated products of fused polycyclic aromatic hydrocarbons).

Examples of the bridged compounds (A3-1a) include, but are not limited to, bicyclic, tricyclic, or tetracyclic bridged hydrocarbons and bridged heterocyclic compounds, such as decahydronaphthalene, bicyclo[2.2.0]hexane, bicyclo[2.2.2] octane, bicyclo[3.2.1]octane, bicyclo[4.3.2]undecane, bicyclo[3.3.3]undecane, thujone, carane, pinane, pinene, bornane, bornylene, norbornane, norbornene, camphor, camphoric acid, camphene, tricyclene, tricyclo[5.2.1.0$^{3,8}$] decane, tricyclo[4.2.1.1$^{2,5}$]decane, exo-tricyclo[5.2.1.0$^{2,6}$] decane, endo-tricyclo[5.2.1.0$^{2,6}$]decane, tricyclo[4.3.1.1$^{2,5}$] undecane, tricyclo[4.2.2.1$^{2,5}$]undecane, endo-tricyclo [5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$]dodecane, perhydroanthracene, perhydroacenaphthene, perhydrophenanthrene, perhydrophenalene, perhydroindene, and quinuclidine; and derivatives of these compounds. These bridged compounds contain a methine carbon atom at a bridgehead position. The bridgehead position corresponds to a junction site when two rings shares two atoms.

Examples of the non-aromatic cyclic compounds (A3-1b) containing a ring and a hydrocarbon group bonded to the ring include, but are not limited to, alicyclic hydrocarbons having 3 to about 15 members and containing a ring and a hydrocarbon group bonded to the ring, such as 1-methylcyclopentane, 1-methylcyclohexane, limonene, menthene, menthol, carvomenthone, and menthone; and derivatives of these compounds. The hydrocarbon group may contain 1 to about 20 (preferably 1 to 10) carbon atoms and are exemplified by alkyl groups. The non-aromatic cyclic compounds (A3-1b) containing a ring and a hydrocarbon group bonded to the ring contain a methine carbon atom at the bonding site between the ring and the hydrocarbon group.

Examples of the chain compounds (A3-2) containing a methine carbon atom include chain hydrocarbons containing a tertiary carbon atom, which are exemplified by, but are not limited to, aliphatic hydrocarbons (or branched chain alkanes) containing 4 to about 20 (preferably, 4 to 10) carbon atoms, such as isobutane, isopentane, 2-methylpentane, 3-methylpentane, 2,2-dimethylbutane, 2,3-dimethylbutane, 3-methylhexane, 3-ethylheptane, 2,2-dimethylpentane, 2,3-dimethylpentane, 2,4-dimethylpentane, 2,2,3-trimethylbutane, 2-methylheptane, 3-methylheptane, 4-methylheptane, 3-ethylhexane, 2,3-dimethylhexane, 2,4-dimethylhexane, 2,5-dimethylhexane, 3,4-dimethylhexane, 3-ethyl-2-methylpentane, 2,2,3-trimethylpentane, 2,2,4-trimethylpentane, 2,3,3-trimethylpentane, and 2,3,4-trimethylpentane; and derivatives of these compounds.

The compounds (A4) containing an unsaturated bond and a carbon-hydrogen bond at an adjacent position to the unsaturated bond include, but are not limited to, (A4-1) aromatic compounds containing an aromatic ring and a methyl and/or methylene group at an adjacent position to the aromatic ring (at the so-called benzyl position); and (A4-2) non-aromatic compounds containing an unsaturated bond and a methyl and/or methylene group at an adjacent position to the unsaturated bond. The unsaturated bond is exemplified by, but is not limited to, carbon-carbon unsaturated bonds such as carbon-oxygen double bond.

The aromatic ring in the aromatic compounds (A4-1) may be any of aromatic hydrocarbon rings and aromatic heterocyclic (heteroaromatic) rings. Examples of the aromatic hydrocarbon rings include benzene ring; and fused carbon rings. Examples of the fused carbon rings include, but are not limited to, fused carbon rings each including two to ten fused 4- to 7-membered carbon rings, such as naphthalene, azulene, indacene, anthracene, phenanthrene, triphenylene, and pyrene. Examples of the heteroaromatic rings include, but are not limited to, heterocyclic rings containing oxygen as a heteroatom(s), such as furan, oxazole, isoxazole, and other 5-membered rings, 4-oxo-4H-pyran and other 6-membered rings, and benzofuran, isobenzofuran, 4-oxo-4H-chromene, and other fused rings; heterocyclic rings containing sulfur as a heteroatom(s), such as thiophene, thiazole, isothiazole, thiadiazole, and other 5-membered rings, 4-oxo-4H-thiopyran and other 6-membered rings, and benzothiophene and other fused rings; and heterocyclic rings containing nitrogen as a heteroatom(s), such as pyrrole, pyrazole, imidazole, triazole, and other 5-membered rings, pyridine, pyridazine, pyrimidine, pyrazine, and other 6-membered rings, and indole, quinoline, acridine, naphthyridine, quinazoline, purine, and other fused rings.

The methylene group at an adjacent position to the aromatic ring may be a methylene group constituting a non-aromatic ring fused to the aromatic ring. The aromatic compounds (A4-1) may contain both a methyl group and a methylene group at an adjacent position(s) to the aromatic ring.

Examples of the aromatic compounds containing a methyl group at an adjacent position to the aromatic ring include, but are not limited to, aromatic hydrocarbons containing an aromatic ring and one to about six methyl groups substituted on the aromatic ring, such as toluene, o-xylene, m-xylene, p-xylene, o-t-butyltoluene, m-t-butyltoluene, p-t-butyltoluene, 1-ethyl-4-methylbenzene, 1-ethyl-3-methylbenzene, cumene, 1-isopropyl-4-methylbenzene, 1-t-butyl-4-methylbenzene, 1-methoxy-4-methylbenzene, mesitylene, pseudocumene, durene, methylnaphthalene, dimethylnaphthalene, methylanthracene, 4,4'-dimethylbiphenyl, tolualdehyde, dimethylbenzaldehyde, trimethylbenzaldehydes, toluic acids, trimethylbenzoic acids, and dimethylbenzoic acids; and heterocyclic compounds containing a heterocyclic ring and one to about six methyl groups substituted on the heterocyclic ring, such as 2-methylfuran, 3-methylfuran, 3-methylthiophene, 2-methylpyridine, 3-methylpyridine, 4-methylpyridine, 2,4-dimethylpyridine, 2,4,6-trimethylpyridine, 4-methylindole, 2-methylquinoline, and 3-methylquinoline.

Examples of the aromatic compounds containing an aromatic ring and a methylene group at an adjacent position to the aromatic ring include, but are not limited to, aromatic hydrocarbons containing alkyl or substituted alkyl containing two or more carbon atoms, such as ethylbenzene, propylbenzene, butylbenzene, 1,4-diethylbenzene, and diphenylmethane; heteroaromatic compounds containing alkyl or substituted alkyl containing two or more carbon atoms, such as 2-ethylfuran, 3-propylthiophene, 4-ethylpyridine, and 4-butylquinoline; and compounds containing an aromatic ring fused to a non-aromatic ring and having a methylene group at a position in the non-aromatic ring adjacent to the aromatic ring, such as dihydronaphthalene, indene, indane, tetrahydronaphthalene, fluorene, acenaphthene, phenalene, indanone, and xanthene.

Examples of the non-aromatic compounds (A4-2) containing an unsaturated bond and a methyl and/or methylene group at an adjacent position to the unsaturated bond include, but are not limited to, (A4-2a) chain unsaturated hydrocarbons containing a methyl and/or methylene group at a so-called allyl position; and (A4-2b) compounds containing a carbonyl group and a methyl and/or methylene group at an adjacent position to the carbonyl group.

Examples of the chain unsaturated hydrocarbons (A4-2a) include, but are not limited to, chain unsaturated hydrocarbons containing 3 to about 20 carbon atoms, such as propylene, 1-butene, 2-butene, 1-pentene, 1-hexene, 2-hexene, 1,5-hexadiene, 1-octene, 3-octene, and undecatrienes. Examples of the compounds (A4-2b) include, but are not limited to, ketones including chain ketones such as acetone, methyl ethyl ketone, 3-pentanone, and acetophenone, and cyclic ketones such as cyclohexanone; and carboxylic acids and derivatives thereof, such as acetic acid, propionic acid, butanoic acid, pentanoic acid, hexanoic acid, heptanoic acid, phenylacetic acid, malonic acid, succinic acid, glutaric acid, and esters of these carboxylic acids.

The alicyclic compounds (i.e., non-aromatic cyclic hydrocarbons) (A5) include, but are not limited to, (A5-1) cycloalkanes and (A5-2) cycloalkenes.

Examples of the cycloalkanes (A5-1) include, but are not limited to, compounds having a cycloalkane ring containing 3 to 30 members (preferably 5 to 30 members, and particularly preferably 5 to 20 members), such as cyclopropane, cyclobutane, cyclopentane, cyclohexane, cycloheptane, cyclooctane, cyclononane, cyclodecane, cyclododecane, cyclotetradecane, cyclohexadecane, cyclotetracosane, and cyclotriacontane; and derivatives of these compounds.

Examples of the cycloalkenes (A5-2) include, but are not limited to, compounds having a cycloalkene ring containing 3 to 30 members (preferably 3 to 20-membered rings, and particularly preferably 3 to 12 members), such as cyclopropene, cyclobutene, cyclopentene, cyclooctene, cyclohexene, 1-methyl-cyclohexene, isophorone, cycloheptene, and cyclododecene; cycloalkadienes such as cyclopentadiene, 1,3-cyclohexadiene, and 1,5-cyclooctadiene; cycloalkatrienes such as cyclooctatrienes; and derivatives of these compounds.

Examples of the conjugated compounds (A6) include, but are not limited to, conjugated dienes (A6-1), $\alpha,\beta$-unsaturated nitriles (A6-2), $\alpha,\beta$-unsaturated carboxylic acids and derivatives thereof (e.g., esters, amides, and acid anhydrides) (A6-3).

Examples of the conjugated dienes (A6-1) include, but are not limited to, butadiene, isoprene, 2-chlorobutadiene, and 2-ethylbutadiene. The "conjugated dienes (A6-1)" also include vinylacetylene and other compounds in which a double bond and a triple bond are conjugated to each other.

Non-limiting examples of the $\alpha,\beta$-unsaturated nitriles (A6-2) include (meth)acrylonitrile.

Examples of the $\alpha,\beta$-unsaturated carboxylic acids and derivative thereof (A6-3) include, but are not limited to, (meth)acrylic acid; (meth)acrylic esters such as methyl (meth)acrylate, ethyl (meth)acrylate, isopropyl (meth)acrylate, butyl (meth)acrylate, and 2-hydroxyethyl (meth)acrylate; and (meth)acrylamide and (meth)acrylamide derivatives such as N-methylol(meth)acrylamide.

Examples of the amine compounds (A7) include, but are not limited to, primary or secondary amines including aliphatic amines such as methylamine, ethylamine, propylamine, butylamine, dimethylamine, diethylamine, dibutylamine, ethylenediamine, 1,4-butanediamine, hydroxyamine, and ethanolamine; alicyclic amines such as cyclopentylamine and cyclohexylamine; aromatic amines such as benzylamine and toluidine; cyclic amines, to which an aromatic or non-aromatic ring may be fused, such as pyrrolidine, piperidine, piperazine, and indoline.

Examples of the aromatic compounds (A8) include, but are not limited to, aromatic hydrocarbons containing at least one benzene ring, such as benzene, naphthalene, acenaphthylene, phenanthrene, anthracene, and naphthacene; and fused polycyclic aromatic hydrocarbons containing two or more (e.g., two to ten) fused benzene rings. To the benzene ring(s), any of non-aromatic carbon rings, heteroaromatic rings, and non-heteroaromatic rings may be fused. These aromatic compounds may have one or more substituents. Examples of the substituted aromatic compounds include, but are not limited to, 2-chloronaphthalene, 2-methoxynaphthalene, 1-methylnaphthalene, 2-methylnaphthalene, 1-bromoanthracene, 2-methylanthracene, 2-t-butylanthracene, 2-carboxyanthracene, 2-ethoxycarbonylanthracene, 2-cyanoanthracene, 2-nitroanthracene, and 2-methylpentalene.

Examples of the normal alkanes (linear alkanes) (A9) include, but are not limited to, normal alkanes containing 1 to about 30 carbon atoms (preferably 1 to 20 carbon atoms), such as methane, ethane, propane, butane, pentane, hexane, heptane, octane, nonane, decane, dodecane, tetradecane, and hexadecane.

Examples of the olefins (A10) include $\alpha$-olefins, internal olefins, and dienes and other olefins each containing two or more carbon-carbon double bonds. Each of these olefins may have one or more substituents such as hydroxy and acyloxy. Specifically, examples of the olefins include, but are not limited to, chain olefins such as ethylene, propylene, 1-butene, 2-butene, isobutene, 1-hexene, 2-hexene, 1-acetoxy-3,7-dimethyl-2,6-octadiene, styrene, vinyltoluene, $\alpha$-methylstyrene, 3-vinylpyridine, and 3-vinylthiophene; and cyclic olefins such as cyclopentene, cyclohexene, cycloheptene, cyclooctene, cyclodecene, cyclododecene, 1,4-cyclohexadiene, limonene, 1-p-menthene, 3-p-menthene, carveol, bicyclo[2.2.1]hept-2-ene, bicyclo[3.2.1]oct-2-ene, $\alpha$-pinene, and 2-bornene.

Each of the substrates (A) may be used alone, or two or more substrates (A) of identical or different categories may be used in combination. The present invention uses oxygen as an oxidizer in the coexistence of ozone. This configuration allows the substrate to be oxidized with very excellent oxidizing power. Accordingly, even normal alkanes (A9), which are generally believed to be resistant to oxidation, can be efficiently oxidized to yield corresponding oxides in high yields.

Gasoline, which mainly includes three components, i.e., 2,2,4-trimethylpentane, n-heptane, and toluene, can be oxidized using the oxidation reaction according to the present invention to have a higher octane number. This may contribute to more efficient combustion of the gasoline. Specifically, the oxide production method according to the present invention is particularly useful as a gasoline reforming method.

Radical Generator

In the present invention, the oxidation reaction is preferably performed further in the presence of a radical generator, where the radical generator is capable of forming an active radical species that abstracts hydrogen from the imide compound. This configuration is preferred for a still higher reaction rate.

The radical generator may be selected from, without limitation, compounds generally used as radical generators. Among them, the radical generator for use in the present invention is preferably at least one selected from nitric acid and nitrogen oxides contained typically in an exhaust gas. Advantageously, this configuration can reduce the exhaust gas, can reduce the environmental load, and still allows the oxidation reaction to be performed more satisfactorily. Examples of the nitrogen oxides include, but are not limited to, nitrogen monoxide (NO), nitrogen dioxide ($NO_2$), dinitrogen monoxide ($N_2O$), dinitrogen trioxide ($N_2O_3$), dinitrogen tetroxide ($N_2O_4$), and dinitrogen pentoxide ($N_2O_5$).

The at least one selected from nitric acid and nitrogen oxides may be used in an amount of typically about 0.001 to about 50 moles, and preferably 0.01 to 10 moles, per mole of the substrate (A). When two or more selected from nitric acid and nitrogen oxides are used, the term "amount" refers to the total amount of them.

The at least one of nitric acid and nitrogen oxides may be added at once upon charging of materials, or may be added to the reaction system continuously or intermittently.

Oxidation Reaction

According to present invention, the oxidation reaction can proceed smoothly even under mild conditions. The reaction temperature can be selected as appropriate according typically to the type of the substrate (A) and the type of the target product (e.g., an alcohol, a ketone, and/or a diketone) and is typically from room temperature to about 200° C., preferably 50° C. to 130° C., and particularly preferably 60° C. to 100° C. Since the oxidation reaction has the configuration, the present invention can efficiently oxidize substrate normal alkanes, which are resistant to oxidation, even in a mild environment at a temperature of 100° C. or lower and can give corresponding oxides in high yields.

The oxidation reaction in the present invention can be performed under normal atmospheric pressure or under pressure (under a load). The oxidation reaction, when performed under pressure, may be performed at a pressure of generally about 0.1 to about 10 MPa, preferably 0.15 to 8 MPa, and particularly preferably 0.5 to 8 MPa. Oxygen is used as an oxidizer in combination with ozone according to the present invention. This configuration allows the oxidation reaction to proceed smoothly even under normal atmospheric pressure (0.1 MPa). The reaction time may be adjusted as appropriate according to the reaction temperature and pressure and is typically about 0.1 to about 20 hours, and preferably 1 to 10 hours. Adjustment of the reaction time within the range can selectively give a target oxide. For example, to selectively produce an alcohol, the reaction time is preferably adjusted to be short (e.g., about 0.5 to about 8.0 hours).

The oxidation reaction may be performed by a common procedure typically of batch system, semi-batch system, or continuous system. Gradual (continuous or intermittent) addition of the imide compound to the system may allow the substrate to be oxidized with a higher conversion and to give an oxide with a higher selectivity. Gradual (continuous or intermittent) addition of the metallic compound as the promoter to the system allows the substrate to be oxidized with a higher conversion and to give an oxide with a higher selectivity.

After the completion of the reaction, the oxide may be separated/purified typically by a separation method such as filtration, concentration, distillation, extraction, crystallization, recrystallization, or column chromatography, or a separation method as any combination of them.

The method according to the present invention can rapidly oxidize the substrate (A) (e.g., substrates that are resistant to oxidation, such as the normal alkanes (A9)) under mild conditions and can efficiently produce a corresponding oxide. The rapid oxidation can be achieved even when, of the imide compounds containing a cyclic imide skeleton represented by Formula (I), one having low solubility (e.g., one having a solubility parameter SP of greater than 26) is used as a catalyst, and even when the oxidation is performed approximately in the absence of solvents.

EXAMPLES

The present invention will be illustrated in further detail with reference to several examples below. It should be noted, however, that the examples are by no means intended to limit the scope of the present invention.

Example 1

A 200-mL four-necked flask was equipped with a thermometer, a gas inlet tube, and a cooling condenser and was charged with tetradecane (supplied by Tokyo Chemical Industry Co., Ltd., 79.36 g, i.e., 104 mL, 400 mmol), N-hydroxysuccinimide (hereinafter also referred to as "NHSI", supplied by Wako Pure Chemical Industries, Ltd., SP: 33.5 $(MPa)^{1/2}$, 4 mmol), cobalt acetylacetonate (supplied by Tokyo Chemical Industry Co., Ltd., 0.4 mmol), and manganese acetate tetrahydrate (supplied by Wako Pure Chemical Industries, Ltd., 0.04 mmol).

A gas used was oxygen containing 1.4 percent by volume of ozone gas. The ozone gas was generated using an ozone generator (trade name SG-01-PSA2, supplied by Sumitomo Precision Products Co., Ltd.). The gas was bubbled at a rate of 2 L/min. to fill the reactor with the gas, and the bubbling was then stopped. The temperature was raised up to 80° C., followed by heating with stirring for 7 hours with intermittent flow of the gas in a gas phase.

The conversion from tetradecane, and the yields of oxides (tetradecanone and tetradecanol) were measured by gas chromatography immediately after the temperature reached 80° C. (zero hour), and 1 hour, 3 hours, and 7 hours thereafter.

Comparative Example 1

A procedure similar to Example 1 was performed, except for using oxygen gas (Sumitomo Seika Chemicals Co., Ltd.) instead of the ozone-gas-containing oxygen gas.

Comparative Example 2

A procedure similar to Example 1 was performed, except for using no NHSI.

Figure 2:
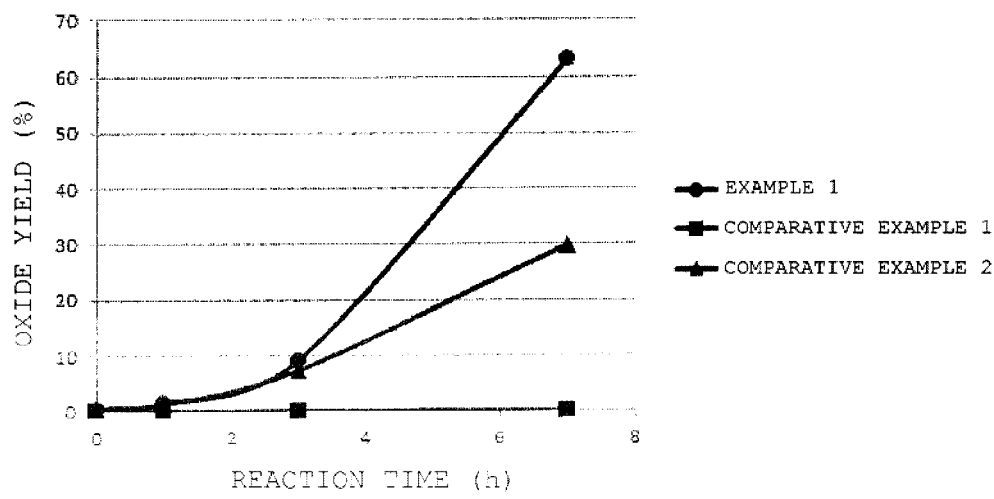
FIG. 2 is a graph illustrating how an oxide yield varies depending on the reaction time in oxidation reactions according to Example 1 and Comparative Examples 1 and 2.

Results are shown in Tables 1 and 2 below and FIGS. 1 and 2.

TABLE 1

| Reaction time (h) | Raw material conversion (%) | | |
| --- | --- | --- | --- |
| | Example 1 | Comparative Example 1 | Comparative Example 2 |
| 0 | 0.7 | <0.1 | 1.0 |
| 1 | 4.14 | <0.1 | 3.7 |
| 3 | 18.3 | <0.1 | 15.1 |
| 7 | 81.8 | <0.1 | 49.7 |

TABLE 2

| Reaction time (h) | Oxide yield (%) | | |
| --- | --- | --- | --- |
| | Example 1 | Comparative Example 1 | Comparative Example 2 |
| 0 | 0.312 | <0.1 | 0.482 |
| 1 | 1.52 | <0.1 | 1.3 |
| 3 | 9.14 | <0.1 | 7.36 |
| 7 | 63.03 | <0.1 | 29.8 |

Example 2

A 200-mL four-necked flask was equipped with a thermometer, a gas inlet tube, and a cooling condenser and was charged with toluene (supplied by Wako Pure Chemical Industries, Ltd., 92.14 g, i.e., 106 mL, 1000 mmol), acetic acid (supplied by NACALAI TESQUE, INC., 10.6 mL), NHSI (2 mmol), and cobalt naphthenate (supplied by Wako Pure Chemical Industries, Ltd., having a cobalt content of about 6.0%, 0.2 mmol in terms of cobalt).

A gas used was oxygen containing 1.4 percent by volume of ozone gas. The ozone gas was generated using an ozone generator (trade name SG-01-PSA2, supplied by Sumitomo Precision Products Co., Ltd.). The gas was bubbled at a rate of 2 L/min. to fill the reactor with the gas, and the bubbling was then stopped. The temperature was raised to 80° C., followed by heating with stirring with intermittent flow of the gas in a gas phase. This gave benzoic acid. The formation of benzyl alcohol and benzaldehyde was not observed, where benzyl alcohol and benzaldehyde are reaction intermediates.

The conversion from toluene, and the oxide (benzoic acid) yield were measured by gas chromatography immediately after the temperature reached 80° C. (zero hour), and 1 hour, 3 hours, and 4 hours thereafter.

Comparative Example 3

A procedure similar to Example 2 was performed, except for using oxygen gas (Sumitomo Seika Chemicals Co., Ltd.) instead of the ozone-gas-containing oxygen gas.

Comparative Example 4

A procedure similar to Example 2 was performed, except for using no NHSI.

Figure 3:
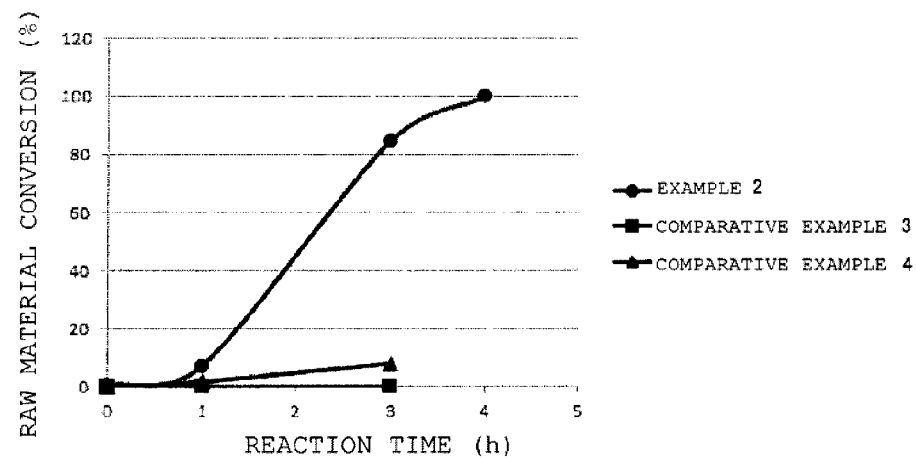
FIG. 3 is a graph illustrating how the raw material conversion varies depending on the reaction time in oxidation reactions according to Example 2 and Comparative Examples 3 and 4.
Figure 4:
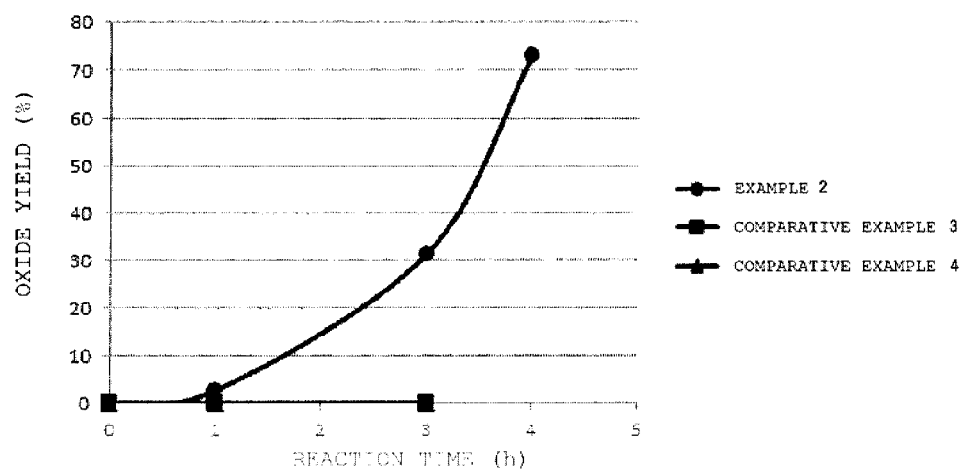
FIG. 4 is a graph illustrating how the oxide yield varies depending on the reaction time in oxidation reactions according to Example 2 and Comparative Examples 3 and 4.

Results are shown in Tables 3 and 4 below and FIGS. 3 and 4.

TABLE 3

| | Raw material conversion (%) | | |
|---|---|---|---|
| Reaction time (h) | Example 2 | Comparative Example 3 | Comparative Example 4 |
| 0 | 0.70 | 0.00 | 1.10 |
| 1 | 7.18 | 0.00 | 1.83 |
| 3 | 84.8 | 0.00 | 8.09 |
| 4 | 100 | — | — |

TABLE 4

| | Oxide yield (%) | | |
|---|---|---|---|
| Reaction time (h) | Example 2 | Comparative Example 3 | Comparative Example 4 |
| 0 | 0.00 | 0.00 | 0.00 |
| 1 | 2.66 | 0.00 | 0.00 |
| 3 | 31.5 | 0.00 | 0.06 |
| 4 | 73.2 | — | — |

Example 3

A 100-mL SUS pressure-tight reactor (supplied by Taiatsu Techno Corporation, Model TVS-1) equipped with a gas flow line and an insertion tube was charged with 0.808 g (4.95 mmol, 10.0 mole percent relative to the substrate) of N-hydroxyphthalimide (hereinafter also referred to as "NHPI", having a solubility parameter SP of 33.4 (MPa)$^{1/2}$), 0.0142 g (0.0495 mmol, 0.1 mole percent relative to the substrate) of manganese acetate tetrahydrate, and 10.0 g (50.4 mmol) of tetradecane (supplied by Tokyo Chemical Industry Co., Ltd.). The reactor was then placed on an oil bath, followed by gas flow line coupling. A gas used was air containing ozone gas. The ozone gas was generated using an ozone generator (trade name SG-01-PSA2, supplied by Sumitomo Precision Products Co., Ltd.). The gas (air) had an oxygen content of 20.7 percent by volume and an ozone gas content of 0.3 percent by volume. Bubbling of the gas (air) at a rate of 1000 mL/min. was started. Heating of the reactor was started, and, at the time when the internal temperature reached 90° C., 0.996 g (0.995 mmol in terms of cobalt, 2.0 mole percent relative to the substrate) of cobalt naphthenate (supplied by Wako Pure Chemical Industries, Ltd., having a cobalt content of about 6.0%) was added to start a reaction. The conversion from tetradecane was measured by gas chromatography (column: 007-FFAP) immediately after the reaction start (zero hour), as well as 1 hour, 2 hours, 3 hours, and 4 hours after the reaction start.

Example 4

A 100-mL SUS pressure-tight reactor (supplied by Taiatsu Techno Corporation, Model TVS-1) equipped with a gas flow line and an insertion tube was charged with 0.206 g (1.26 mmol, 2.5 mole percent relative to the substrate) of NHPI, 0.0034 g (0.0013 mmol, 0.025 mole percent relative to the substrate) of manganese acetate tetrahydrate, and 10.0 g (50.4 mmol) of tetradecane (supplied by Tokyo Chemical Industry Co., Ltd.). The reactor was then placed on an oil bath, followed by gas flow line coupling. A gas used herein was air containing ozone gas, where the ozone gas was generated using an ozone generator (trade name SG-01-PSA2, supplied by Sumitomo Precision Products Co., Ltd.). The gas (air) had an oxygen content of 20.7 percent by volume and an ozone gas content of 0.3 percent by volume. Bubbling of the gas (air) at a rate of 1000 mL/min. was started. Heating of the reactor was started, and, at the time when the internal temperature reached 90° C., 0.250 g (0.25 mmol in terms of cobalt, 0.5 mole percent relative to the substrate) of cobalt naphthenate (supplied by Wako Pure Chemical Industries, Ltd., having a cobalt content of about 6.0%) was added to start a reaction. Cobalt naphthenate was added in an amount equal to the initial charge amount (0.25 g, 0.5 mole percent relative to the substrate) every one hour after the reaction start. The conversion from tetradecane was measured by gas chromatography (column: 007-FFAP) immediately after the reaction start (zero hour) and 1 hour, 2 hours, 3 hours, and 4 hours after the reaction start.

Example 5

A procedure similar to Example 4 was performed, except that the air containing ozone gas was fed by flow in a gas phase at a rate of 1000 mL/min. instead of the bubbling.

Figure 5:
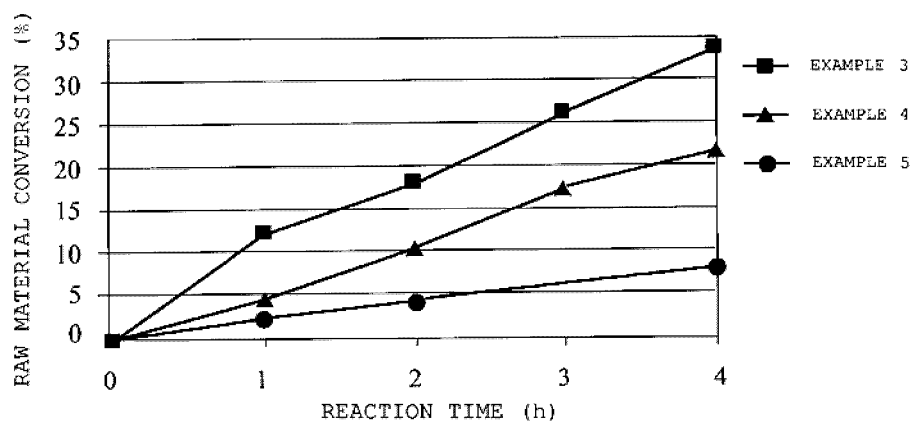
FIG. 5 is a graph illustrating how the raw material conversion varies depending on the reaction time in oxidation reactions according to Examples 3 to 5.

Results are shown in Table 5 below and FIG. 5.

TABLE 5

| | Raw material conversion (%) | | |
|---|---|---|---|
| Reaction time (h) | Example 3 | Example 4 | Example 5 |
| 0 | 0 | 0 | 0 |
| 1 | 12.3 | 4.64 | 2.3 |
| 2 | 18.2 | 10.4 | 4.2 |
| 3 | 26.1 | 17.4 | 6.0 |
| 4 | 33.6 | 21.7 | 8.0 |

Examples 6 to 8

Under conditions given in Table 6 below, NHPI, manganese acetate tetrahydrate (0.01 mole percent relative to the substrate), and tetradecane (supplied by Tokyo Chemical Industry Co., Ltd., 10 g (50.4 mmol)) were placed in a 100-mL SUS pressure-tight reactor (supplied by Taiatsu Techno Corporation, Model TVS-1) equipped with a gas flow line and an insertion tube. The reactor was placed on an oil bath and gas flow line coupling. A gas used was air containing ozone gas, where the ozone gas was generated using an ozone generator (trade name SG-01-PSA2, supplied by Sumitomo Precision Products Co., Ltd.). The gas (air) had an oxygen content of 20.7 percent by volume and an ozone gas content of 0.3 percent by volume. The flow of the gas (air) at a rate of 50 mL/min. in a gas phase was started. Heating of the reactor was started, and, at the time when the internal temperature reached 80° C., cobalt naphthenate (supplied by Wako Pure Chemical Industries, Ltd., having a cobalt content of about 6.0%) was added to start a reaction. In Examples 7 to 9, cobalt naphthenate was further added in an amount equal to the initial charge amount every one hour after the reaction start. The conversion from tetradecane was measured by gas chromatography (column: 007-FFAP) immediately after the reaction start (zero hour), and 1 hour, 2 hours, 3 hours, and 4 hours after the reaction start.

Example 9

A procedure similar to Examples 6 to 8 was performed, except for using manganese acetate tetrahydrate in an amount of 0.25 mole percent relative to the substrate.

TABLE 6

| | NHPI charge amount (mol %) | Cobalt naphthenate initial charge amount (mol %) times number of charging | Cobalt naphthenate total charge amount (mol %) | Ratio (molar ratio) of NHPI to cobalt naphthenate |
|---|---|---|---|---|
| Example 6 | 1.0 | 0.1 mol % × 1 | 0.1 | 1:0.1 |
| Example 7 | 1.0 | 0.5 mol % × 4 | 2.0 | 1:0.5 |
| Example 8 | 1.0 | 0.2 mol % × 4 | 0.8 | 1:0.2 |
| Example 9 | 2.5 | 0.5 mol % × 4 | 2.0 | 1:0.2 |

Figure 6:
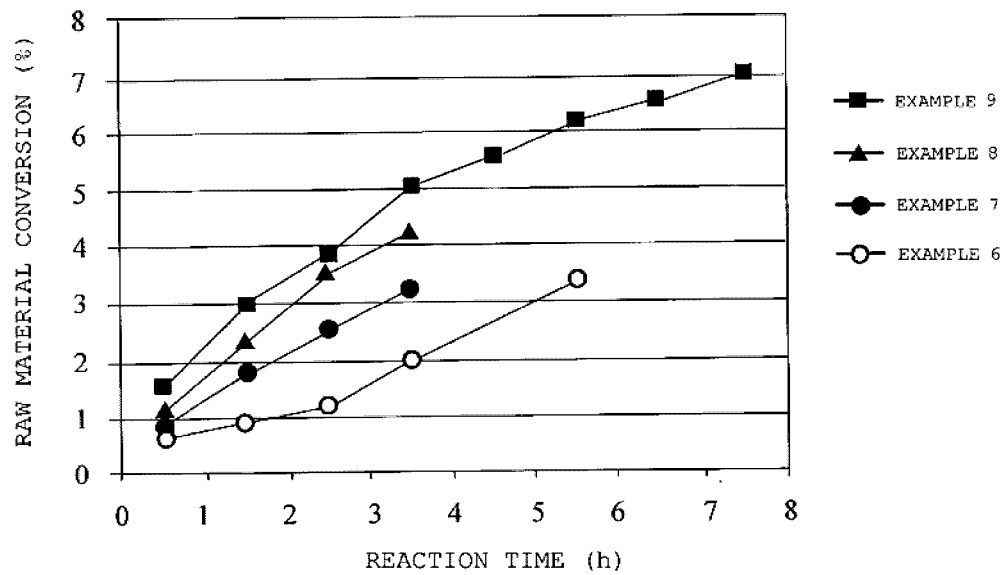
FIG. 6 is a graph illustrating how the raw material conversion varies depending on the reaction time in oxidation reactions according to Examples 6 to 9.

Results are shown in Table 7 below and FIG. 6.

TABLE 7

| | Raw material conversion (%) | | | |
|---|---|---|---|---|
| Reaction time (h) | Example 6 | Example 7 | Example 8 | Example 9 |
| 0 | 0 | 0 | 0 | 0 |
| 1 | 0.6 | 0.9 | 1.1 | 1.6 |
| 2 | 0.9 | 1.8 | 2.4 | 3 |
| 3 | 1.2 | 2.6 | 3.7 | 3.9 |
| 4 | 2 | 3.3 | 4.3 | 5.1 |

Example 10

A 300-mL four-necked flask was equipped with a thermometer and a cooling condenser and was charged with tetradecane (supplied by Tokyo Chemical Industry Co., Ltd., 79.36 g, i.e., 104 mL, 400 mmol), NHPI (1 mole percent relative to the substrate), cobalt naphthenate (supplied by Wako Pure Chemical Industries, Ltd., having a cobalt content of about 6.0%, 1 mole percent in terms of cobalt relative to the substrate), and manganese acetate tetrahydrate (supplied by Wako Pure Chemical Industries, Ltd., 0.1 mole percent relative to the substrate).

$NO_2$ gas in an amount of 10 mole percent relative to the substrate was bubbled, followed by heating start. Two hours and four hours into heating, $NO_2$ gas in the equivalent amount was further added.

Further, bubbling (1000 mL/min.) of oxygen containing 1.4 percent by volume of ozone gas was started. The temperature of the reactor was raised until the internal temperature reached 80° C., held at that temperature (80° C.) for 4 hours, then further raised to 110° C., followed by stirring for 4 hours while being held at that temperature (110° C.). The conversion from tetradecane was measured by gas chromatography (column: DB-1) immediately after the reaction start (zero hour), and 1 hour, 2 hours, 3 hours, 4 hours, and 8 hours after the reaction start.

Example 11

A procedure similar to Example 10 was performed, except that concentrated nitric acid (containing $HNO_3$ in a content of 98% or more) was added in an amount in terms of $HNO_3$ of 10 mole percent relative to the substrate at once at the reaction start, instead of the intermittent $NO_2$ gas addition.

Comparative Example 5

A procedure similar to Example 10 was performed, except for using oxygen gas (Sumitomo Seika Chemicals Co., Ltd.) instead of the ozone-gas-containing oxygen gas, and not using the $NO_2$ gas.

Results are shown in Table 8 below.

TABLE 8

| Reaction temperature (° C.) | Reaction time (h) | Raw material conversion (%) | | |
|---|---|---|---|---|
| | | Example 10 | Example 11 | Comparative Example 5 |
| 80° C. | 0 | 0 | 0 | 0 |
| | 1 | 0.5 | 1 | 0 |
| | 2 | 1.5 | 2.5 | 0 |
| | 4 | 3 | 5 | 0 |
| 110° C. | 8 | 9 | 10 | 0 |

Example 12

A 500-mL SUS pressure-tight reactor (supplied by Fuji Techno Engineering Corporation) was charged with tetradecane (supplied by Tokyo Chemical Industry Co., Ltd., 357 mmol), NHPI (8.93 mmol), cobalt naphthenate (supplied by Wako Pure Chemical Industries, Ltd., having a cobalt content of about 6.0%, 1.79 mmol in terms of cobalt), and manganese acetate tetrahydrate (supplied by Wako Pure Chemical Industries, Ltd., 0.089 mmol).

A gas used was air containing ozone gas, where the ozone gas was generated using an ozone generator (trade name SG-01-PSA2, supplied by Sumitomo Precision Products Co., Ltd.). The gas (air) had an oxygen content of 20.7 percent by volume and an ozone gas content of 0.3 percent by volume. The gas (air) was bubbled at a rate of 2000 mL/min. to fill the reactor with the gas, and the bubbling was stopped. The temperature was raised to 95° C. with intermittent flow of the gas in a gas phase, followed by heating with stirring for 4 hours. The conversion from the substrate was measured by gas chromatography (column: 007-FFAP) and found to be 16%.

Comparative Example 6

A procedure similar to Example 12 was performed, except for using air without the addition of ozone gas, instead of the ozone-gas-added air. As a result, the conversion from the substrate was found to be 6.6%.

Example 13

A procedure similar to Example 12 was performed, except for using 2,2,4-trimethylpentane (569 mmol) as the substrate instead of tetradecane. As a result, the conversion from the substrate was found to be 21%.

Comparative Example 7

A procedure similar to Example 13 was performed, except for using air without the addition of ozone gas, instead of the ozone-gas-added air. As a result, the conversion from the substrate was found to be 8.7%.

Example 14

A procedure similar to Example 12 was performed, except for using n-heptane (630 mmol) as the substrate instead of tetradecane. As a result, the conversion from the substrate was found to be 17%.

Comparative Example 8

A procedure similar to Example 14 was performed, except for using air without the addition of ozone gas, instead of the ozone-gas-added air. As a result, the conversion from the substrate was found to be 6.9%.

Example 15

A procedure similar to Example 12 was performed, except for using toluene (798 mmol) as the substrate instead of tetradecane. As a result, the conversion from the substrate was found to be 100%.

Comparative Example 9

A procedure similar to Example 15 was performed, except for using air without the addition of ozone gas, instead of the ozone-gas-added air. As a result, the conversion from the substrate was found to be 43%.

Example 16

A procedure similar to Example 12 was performed, except for using cyclohexane (833 mmol) as the substrate instead of tetradecane. As a result, the conversion from the substrate was found to be 25%.

Comparative Example 10

A procedure similar to Example 16 was performed, except for using air without the addition of ozone gas, instead of the ozone-gas-added air. As a result, the conversion from the substrate was found to be 10.4%.

Example 17

A procedure similar to Example 12 was performed, except for using cyclohexene (889 mmol) as the substrate instead of tetradecane. As a result, the conversion from the substrate was found to be 30%.

Comparative Example 11

A procedure similar to Example 17 was performed, except for using air without the addition of ozone gas, instead of the ozone-gas-added air. As a result, the conversion from the substrate was found to be 13%.

Example 18

A procedure similar to Example 12 was performed, except for using isochroman (716 mmol) as the substrate instead of tetradecane. As a result, the conversion from the substrate was found to be 40%.

Comparative Example 12

A procedure similar to Example 18 was performed, except for using air without the addition of ozone gas, instead of the ozone-gas-added air. As a result, the conversion from the substrate was found to be 17%.

Example 19

A procedure similar to Example 12 was performed, except for using cumene (647 mmol) as the substrate instead of tetradecane. As a result, the conversion from the substrate was found to be 35%.

Comparative Example 13

A procedure similar to Example 19 was performed, except for using air without the addition of ozone gas, instead of the ozone-gas-added air. As a result, the conversion from the substrate was found to be 15%.

INDUSTRIAL APPLICABILITY

With the oxide production method according to the present invention, a corresponding oxide can be produced in a high yield from a substrate under mild conditions, even when a commercially available imide compound is used as intact as a catalyst, even when a normal alkane, which is resistant to oxidation, is used as the substrate, and/or even when the oxidation is performed approximately in the absence of solvents.

The present invention is therefore applicable typically to fuel reforming by promoting oxidation of hydrocarbons, sulfides, inorganic components, and any other components in fuels such as gasoline; oxygen gas purification by oxidizing carbon monoxide in the oxygen gas; oxidative removal of hydrocarbons from silicon oxides; removal of nitrogen oxides from internal atmosphere of Diesel engines; and exhaust gas purification by oxidative removal of hydrocarbons and carbon monoxide from the exhaust gas.

The invention claimed is:
1. A method for producing an oxide, the method comprising
performing oxidation of a substrate (A) in the presence of oxygen and ozone under catalysis of an imide com- pound to yield the corresponding oxide, the imide compound containing a cyclic imide skeleton represented by Formula (I):

[Chem. 1]

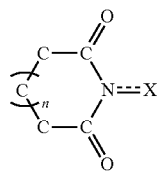

(I)

wherein n is selected from 0 and 1; and X is selected from an oxygen atom and an —OR group, where R is selected from hydrogen and a hydroxy-protecting group,
  the substrate (A) including a compound selected from the group consisting of:
  (A1) compounds containing a heteroatom and a carbon-hydrogen bond at an adjacent position to the heteroatom;
  (A2) compounds containing a carbon-heteroatom double bond;
  (A3) compounds containing a methine carbon atom;
  (A4) compounds containing an unsaturated bond and a carbon-hydrogen bond at an adjacent position to the unsaturated bond;
  (A5) alicyclic compounds;
  (A6) conjugated compounds;
  (A7) amine compounds;
  (A8) aromatic compounds;
  (A9) normal alkanes; and
  (A10) olefins.

2. The method according to claim 1 for producing an oxide,
  wherein a metallic compound is used as a promoter in combination with the imide compound as a catalyst.

3. The method according to claim 2 for producing an oxide,
  wherein the metallic compound includes at least one metal element selected from the group consisting of cobalt, manganese, zirconium, and molybdenum.

4. The method according to claim 1 for producing an oxide,
  wherein the oxidation as a reaction is performed using approximately no solvent.

5. The method according to claim 1 for producing an oxide,
  wherein the oxidation as a reaction is performed under normal atmospheric pressure.

6. The method according to claim 1 for producing an oxide,
  wherein the oxidation as a reaction is performed in the presence of at least one selected from the group consisting of nitric acid and nitrogen oxides.

7. The method according to claim 1 for producing an oxide,
  wherein the oxidation as a reaction is performed at a temperature of 100° C. or lower.

8. A method for oxidizing a substrate, the method comprising
  oxidizing a substrate (A) in the presence of oxygen and ozone under catalysis of an imide compound, the imide compound containing a cyclic imide skeleton represented by Formula (I):

[Chem. 2]

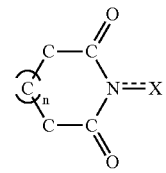

(I)

wherein n is selected from 0 and 1; and X is selected from an oxygen atom and an —OR group, where R is selected from hydrogen and a hydroxy-protecting group,
  the substrate (A) including a compound selected from the group consisting of:
  (A1) compounds containing a heteroatom and a carbon-hydrogen bond at an adjacent position to the heteroatom;
  (A2) compounds containing a carbon-heteroatom double bond;
  (A3) compounds containing a methine carbon atom;
  (A4) compounds containing an unsaturated bond and a carbon-hydrogen bond at an adjacent position to the unsaturated bond;
  (A5) alicyclic compounds;
  (A6) conjugated compounds;
  (A7) amine compounds;
  (A8) aromatic compounds;
  (A9) normal alkanes; and
  (A10) olefins.

9. An oxidation reaction apparatus comprising a reactor for oxidizing a substrate (A) in the presence of oxygen and ozone under catalysis of an imide compound containing a cyclic imide skeleton represented by Formula (I):

[Chem. 1]

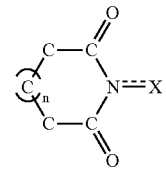

(I)

wherein n is selected from 0 and 1; and X is selected from an oxygen atom and an —OR group, where R is selected from hydrogen and a hydroxy-protecting group,
  the substrate (A) including a compound selected from the group consisting of:
  (A1) compounds containing a heteroatom and a carbon-hydrogen bond at an adjacent position to the heteroatom;
  (A2) compounds containing a carbon-heteroatom double bond;
  (A3) compounds containing a methine carbon atom;
  (A4) compounds containing an unsaturated bond and a carbon-hydrogen bond at an adjacent position to the unsaturated bond;
  (A5) alicyclic compounds;
  (A6) conjugated compounds;
  (A7) amine compounds;
  (A8) aromatic compounds;
  (A9) normal alkanes; and
  (A10) olefins.

10. The method according to claim 2 for producing an oxide,
wherein the oxidation as a reaction is performed using approximately no solvent.

11. The method according to claim 3 for producing an oxide,
wherein the oxidation as a reaction is performed using approximately no solvent.

12. The method according to claim 2 for producing an oxide,
wherein the oxidation as a reaction is performed under normal atmospheric pressure.

13. The method according to claim 3 for producing an oxide,
wherein the oxidation as a reaction is performed under normal atmospheric pressure.

14. The method according to claim 4 for producing an oxide,
wherein the oxidation as a reaction is performed under normal atmospheric pressure.

15. The method according to claim 10 for producing an oxide,
wherein the oxidation as a reaction is performed under normal atmospheric pressure.

16. The method according to claim 11 for producing an oxide,
wherein the oxidation as a reaction is performed under normal atmospheric pressure.

17. The method according to claim 2 for producing an oxide,
wherein the oxidation as a reaction is performed in the presence of at least one selected from the group consisting of nitric acid and nitrogen oxides.

18. The method according to claim 3 for producing an oxide,
wherein the oxidation as a reaction is performed in the presence of at least one selected from the group consisting of nitric acid and nitrogen oxides.

19. The method according to claim 4 for producing an oxide,
wherein the oxidation as a reaction is performed in the presence of at least one selected from the group consisting of nitric acid and nitrogen oxides.

20. The method according to claim 5 for producing an oxide,
wherein the oxidation as a reaction is performed in the presence of at least one selected from the group consisting of nitric acid and nitrogen oxides.

* * * * *